US008324174B2

(12) United States Patent
Smyth et al.

(10) Patent No.: US 8,324,174 B2
(45) Date of Patent: *Dec. 4, 2012

(54) COMPOUNDS FOR ENZYME INHIBITION

(75) Inventors: Mark S. Smyth, Foster City, CA (US);
Guy J. Laidig, Menlo Park, CA (US);
Ronald T. Borchardt, Lawrence, KS (US); Barry A. Bunin, San Mateo, CA (US); Craig M. Crews, New Haven, CT (US); John H. Musser, San Carlos, CA (US)

(73) Assignee: Onyx Therapeutics, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/334,372

(22) Filed: Dec. 22, 2011

(65) Prior Publication Data

US 2012/0101050 A1 Apr. 26, 2012

Related U.S. Application Data

(63) Continuation of application No. 11/578,626, filed as application No. PCT/US2005/012740 on Apr. 14, 2005, now Pat. No. 8,129,346.

(60) Provisional application No. 60/620,573, filed on Oct. 20, 2004, provisional application No. 60/610,159, filed on Sep. 14, 2004, provisional application No. 60/610,002, filed on Sep. 14, 2004, provisional application No. 60/610,001, filed on Sep. 14, 2004, provisional application No. 60/599,401, filed on Aug. 6, 2004, provisional application No. 60/569,096, filed on May 7, 2004, provisional application No. 60/562,340, filed on Apr. 15, 2004.

(51) Int. Cl.
*A61K 38/06* (2006.01)
*C07K 5/10* (2006.01)
*C07K 1/00* (2006.01)

(52) U.S. Cl. .................. 514/21.9; 530/330; 530/333

(58) Field of Classification Search .................. None
See application file for complete search history.

(56) References Cited

U.S. PATENT DOCUMENTS

| | | |
|---|---|---|
| 4,733,665 A | 3/1988 | Palmaz |
| 5,071,957 A | 12/1991 | Konishi et al. |
| 5,134,127 A | 7/1992 | Stella et al. |
| 5,135,919 A | 8/1992 | Folkman et al. |
| 5,340,736 A | 8/1994 | Goldberg |
| 5,376,645 A | 12/1994 | Stella et al. |
| 5,441,944 A | 8/1995 | Weisz et al. |
| 5,874,418 A | 2/1999 | Stella et al. |
| 6,046,177 A | 4/2000 | Stella et al. |
| 6,099,851 A | 8/2000 | Weisman et al. |
| 6,133,248 A | 10/2000 | Stella |
| 6,204,257 B1 | 3/2001 | Stella et al. |
| 6,235,717 B1 | 5/2001 | Leban et al. |
| 6,410,512 B1 | 6/2002 | Mundy et al. |
| 6,462,019 B1 | 10/2002 | Mundy et al. |
| 6,492,333 B1 | 12/2002 | Mundy |
| 6,613,541 B1 | 9/2003 | Vaddi et al. |
| 6,617,309 B2 | 9/2003 | Tung et al. |
| 6,656,904 B2 | 12/2003 | Mundy et al. |
| 6,831,099 B1 | 12/2004 | Crews et al. |
| 6,838,252 B2 | 1/2005 | Mundy et al. |
| 6,838,436 B1 | 1/2005 | Mundy et al. |
| 6,884,769 B1 | 4/2005 | Mundy et al. |
| 6,902,721 B1 | 6/2005 | Mundy et al. |
| 7,232,818 B2 | 6/2007 | Smyth et al. |
| 7,388,017 B2 | 6/2008 | Tung et al. |
| 7,417,042 B2 | 8/2008 | Smyth et al. |
| 7,491,704 B2 | 2/2009 | Smyth et al. |
| 7,687,456 B2 | 3/2010 | Zhou et al. |
| 7,691,852 B2 | 4/2010 | Shenk et al. |
| 7,737,112 B2 | 6/2010 | Lewis et al. |
| 2003/0224469 A1 | 12/2003 | Buchholz et al. |
| 2003/0236223 A1 | 12/2003 | Wagner et al. |
| 2004/0106539 A1 | 6/2004 | Schubert et al. |
| 2004/0266664 A1 | 12/2004 | Crews et al. |
| 2005/0101781 A1 | 5/2005 | Agoulnik et al. |
| 2005/0245435 A1 | 11/2005 | Smyth et al. |
| 2005/0256324 A1 | 11/2005 | Laidig et al. |
| 2006/0030533 A1 | 2/2006 | Smyth et al. |
| 2006/0088471 A1 | 4/2006 | Bennett et al. |
| 2006/0128611 A1 | 6/2006 | Lewis |
| 2006/0241056 A1 | 10/2006 | Orlowski et al. |
| 2007/0105786 A1 | 5/2007 | Zhou et al. |
| 2008/0090785 A1 | 4/2008 | Smyth et al. |

(Continued)

FOREIGN PATENT DOCUMENTS

EP      0 411 660      2/1991

(Continued)

OTHER PUBLICATIONS

"Definition of Cancer," [Retrieved from] http://www.medterms.com, 1 page [retrieved on Sep. 16, 2005]. Adams et al., "Proteasome Inhibitors: A Novel Class of Potent and Effective Antitumor Agents," Cancer Research, 1999, 59:2615-2622.
Almond et al. "The proteasome: a novel target for cancer chemotherapy" Leukemia, 16(4), 433-443, Apr. 2002.
Argiriadi, "Binding of alkylurea inhibitors to epoxide hydrolase implicates active site tyrosines in substrate activation," J. Biol. Chem., 2000, 275(20):15265-15270.
Bao et al. "PR-39 and PR-11 peptides inhibit ischemia-reperfusion injury by blocking proteasome-mediated IκBα degradation" Am. J. Physiol. Heart Circ. Physiol. 281:H2612-H2618, 2001.
Benedetti et al., "Versatile and Stereoselective Synthesis of Diamino Diol Dipeptide Isosteres, Core Units of Pseudopeptide HIV Protease Inhibitors," J. Org. Chem., 1997, 62:9348-9353.
Berge et al. "Pharmaceutical Salts", J. Pharm. Sci. 66(1), 1-19. Jan. 1977.
Bernier et al. "A Methionine aminopeptidase-2 Inhibitor, PPI-2458, for the treatment of rheumatoid arthritis", PNAS 101(29):10768-73, Jul. 20, 2004.

(Continued)

Primary Examiner — Christina Bradley
(74) Attorney, Agent, or Firm — Fish & Richardson P.C.

(57) ABSTRACT

Peptide-based compounds including heteroatom-containing, three-membered rings efficiently and selectively inhibit specific activities of N-terminal nucleophile (Ntn) hydrolases. The activities of those Ntn having multiple activities can be differentially inhibited by the compounds described. For example, the chymotrypsin-like activity of the 20S proteasome may be selectively inhibited with the inventive compounds. The peptide-based compounds include at least three peptide units, an epoxide or aziridine, and functionalization at the N-terminus. Among other therapeutic utilities, the peptide-based compounds are expected to display anti-inflammatory properties and inhibition of cell proliferation.

27 Claims, No Drawings

U.S. PATENT DOCUMENTS

| | | | |
|---|---|---|---|
| 2009/0131421 A1 | 5/2009 | Smyth et al. |
| 2009/0156473 A1 | 6/2009 | Schubert |
| 2009/0203698 A1 | 8/2009 | Zhou et al. |
| 2009/0215093 A1 | 8/2009 | Bennett et al. |
| 2010/0144648 A1 | 6/2010 | Shenk et al. |
| 2010/0144649 A1 | 6/2010 | Shenk et al. |

FOREIGN PATENT DOCUMENTS

| | | |
|---|---|---|
| EP | 1 136 498 | 9/2001 |
| WO | WO 91/13904 | 9/1991 |
| WO | WO 94/15956 | 7/1994 |
| WO | WO 95/24914 | 9/1995 |
| WO | WO 96/13266 | 5/1996 |
| WO | WO 96/32105 | 10/1996 |
| WO | WO 98/10779 | 3/1998 |
| WO | WO 00/02548 | 1/2000 |
| WO | WO 00/61167 | 10/2000 |
| WO | WO 01/28579 | 4/2001 |
| WO | WO 03/059898 | 7/2003 |
| WO | WO 2005/105827 | 11/2005 |
| WO | WO 2005/111008 | 11/2005 |
| WO | WO 2005/111009 | 11/2005 |
| WO | WO 2006/017842 | 2/2006 |
| WO | WO 2006/045066 | 4/2006 |
| WO | WO 2006/099261 | 9/2006 |
| WO | WO 2007/056464 | 5/2007 |
| WO | WO 2007/067976 | 6/2007 |
| WO | WO 2007/149512 | 12/2007 |
| WO | WO 2008/140782 | 11/2008 |
| WO | WO 2009/045497 | 4/2009 |
| WO | WO 2010/048298 | 4/2010 |

OTHER PUBLICATIONS

Bogyo et al. "Biochemistry", PNAS 94:6629-6634, 1997.
Bougauchi et al., "Catalytic Asymmetric Epoxidation of .alpha., .beta.-Unsaturated Ketones Promoted by Lanthanoid Complexes," J. Am. Chem. Soc., 1997, 119:2329-2330.
Brinkley, Michael "A Brief Survey of Methods for Preparing Protein Conjugates with Dyes, Haptens, and Cross-Linking Reagents", Bioconjug. Chem 3:2-13, 1992.
Brown et al., "Selective Reductions. 37. Asymmetric Reduction of Prochiral Ketones with .beta.-(3-Pinanyl)-9-borabicyclo[3.3.1]nonane," J. Org. Chem., 1985, 50:1384-1394.
Caira, "Crystalline Polymorphism of Organic Compounds," Topics in Current Chemistry, 1998, 198:163-208.
Ciechanover, "The Ubiquitin-Proteasome Proteolytic Pathway," Cell, 1994, 79:13-21.
Cohen, "AIDS Mood Upbeat—For a Change," Science, 1995, 267:959-960.
Collins, Tucker, "Endothelial nuclear factor-κB and the initiation of the atherosclerotic lesion", Lab. Invest. 68(5), 499-508, 1993.
Concise Encyclopedia Chemistry, 1993, p. 490.
Corey et al., "A General, Catalytic, and Enantioselective Synthesis of .alpha.-Amino Acids," J. Am. Chem. Soc., 1992, 114:1906-1908.
Corey et al., "Highly Enantioselective Borane Reduction of Ketones Catalyzed by Chiral Oxazaborolidines. Mechanism and Synthetic Implications," J. Am. Chem. Soc., 1987, 109:5551-5553.
Craiu et al. "Lactacystin and clasto-lactacystin β-lactone modify multiple proteasome β-subunits and inhibit intracellular protein degradation and major hisotcompatibility complex class I antigen presentation" J. of Biol. Chem. 272(20), 13437-13445, May 16, 1997.
Datta et al., "A Stereoselective Route to Hydroxyethylamine Dipeptide Isosteres," J. Am. Chem. Soc., 2000, 65:7609-7611.
Demo et al., "Antitumor Activity of PR-171, a Novel Irreversible Inhibitor of the Proteasome," Cancer Research, 2007, 67(13):6383-6391.
Dess et al., "A Useful 12-I-5 Triacetoxyperiodinane (the Dess-Martin Periodinane) for the Selective Oxidation of Primary or Secondary Alcohols and a Variety of Related 12-I-5 Species," J. Am. Chem. Soc., 1991, 113:7277-7287.
Dess et al., "Readily Accessible 12-I-5 Oxidant for the Conversion of Primary and Secondary Alcohols to Aldehydes and Ketones," J. Org. Chem., 1983, 48:4155-4156.

Dobler, "Total synthesis of (+)-epopromycin B and its analogues-studies on the inhibition of cellulose biosynthesis," Tetrahedron Letters, 2001, 42(2):215-218.
Elofsson et al., "Towards subunit-specific proteasome inhibitors: synthesis and evaluation of peptide .alpha.',.beta.'-epoxyketones," Chemistry & Biology, 1999, 6:811-822.
Fenteany et al. "A β-lactone related to lactacystin induces neurite outgrowth in a neuroblastoma cell line and inhibits cell cycle progression in an osteosarcoma cell line", PNAS 91:3358-3362, Apr. 1994.
Fox et al. "Organic Chemistry", Publisher: Jones & Bartlett Pub, Published Jun. 15, 2004, Sec. 5-6, pp. 177-178, ISBN-10: 0763721972, ISBN-13: 9780763721978.
Gao et al. "Inhibition of ubiquitin-proteasome pathway—mediated IκBα degradation by a naturally occurring antibacterial peptide" J. Clin. Invest. 106:439-448, 2000.
Garrett et al., "Selective inhibitors of the osteoblast proteasome stimulate bone formation in vivo and in vitro," J Clinical Investigation, 2003, 111:1771-1782.
Golub et al., "Molecular Classification of Cancer: Class Discovery and Class Prediction by Genes Expression Monitoring," Science, 1999, 286:531-537.
Gonzales et al. "Pain relief in chronic pancreatitis by pancreaticojejunostomy. An institutional experience" Arch. Med. Res. 28(3), 387-390, 1997.
Graz University of Technology, "Database of Fluorescent Dyes Properties and Applications" WWW.Fluorophonres.org, 33 pgs, Exhibit B to response filed with US Patent office on Sep. 16, 2008 for U.S. Appl. No. 11/254,541 (now abandoned).
Green et al. "Protective Groups in Organic Synthesis", 2nd ed., Wiley & Sons, Inc., New York (1991).
Griffith et al. "Molecular recognition of angiogenesis inhibitors fumagillin and ovalicin by methionine aminopeptidase", PNAS 95:15183-88, Dec. 1998.
Groll et al., "Crystal Structure of Epoxomicin:20S Proteasome Reveals a Molecular Basis for Selectivity of r¢,â¢-Epoxyketone Proteasome Inhibitors," J. Am. Chem. Soc. 2000, 122:1237-1238.
Gura, "Systems for Identifying New Drugs are Often Faulty," Science, Nov. 7, 1997, 278(5340):1041-1042.
Hanson et al., "Synthesis of New Dipeptide Analogues Containing Novel Ketovinyl and Hydroxyethylidene Isosteres via Grignard Addition to Chiral .alpha.-Amino Aldehydes," J. Org. Chem., 1985, 50:5399-5401.
Harding et al., "Novel Dipeptide Aldehydes are Proteasome Inhibitors and Block the MHC-1 Antigen-Processing Pathway," J. Immunology, 1995, 155:1767-1775.
Hardy, "The secret life of the hair follicle," Trends in Genetics, 1992, 8:55-61.
Harris et al. "Effects of transforming growth factor 3 on bone nodule formation and expression of bone morphogenetic protein 2, osteocalcin, osteopontin, alkaline phosphatase, and type I collagen mRNA in long-term cultures of fetal rat calvarial osteoblasts", J. Bone Miner. Res. 9(6), 855-863, 1994.
Hawley's Condensed Chemical Dictionary, 1993, p. 594.
Haugland, Rosaria "Coupling of Monoclonal Antibodies with Fluorophores", Methods Mol. Biol. 45, 205-221, 1995.
Hilfiker, Ed., Polymorphism in the Pharmaceutical Industry, 2006, pp. 12-15.
Hoffman et al., "Highly Stereoselective Syntheses of syn- and anti-1,2-Amino Alcohols," J. Org. Chem., 2002, 67:1045-1056.
Iqbal et al. "Potent Inhibitors of Proteasome", J. Med Chem. 38:2276-2277, 1995.
Iqbal et al., "Potent .alpha.-ketocarbonyl and boronic ester derived inhibitors of proteasome," Bioorganic & Medicinal Chemistry Letters, 1996, 6:287-290.
Jacobsen et al., "Asymmetric Dihydroxylation via Ligand-Accelerated Catalysis," J. Am. Chem. Soc., 1988, 110:1968-1970.
Jain, "Delivery of Molecular Medicine to Solid Tumors," Science, 1996, 271(5252):1079-1080.
Jones et al., "Total Synthesis of the Immunosuppressant (−)-FK-506," J. Am. Chem. Soc., 1989, 111:1157-1159.

Kessler et al. "Extended peptide-based inhibitors efficiently target the proteasome and reveal overlapping specificities of the catalytic β-subunits", Chem & Biol. 8(9), 913-929, Aug. 8, 2001.

Kim et al., "Proteasome inhibition by the natural products epoxomicin and dihydroeponemycin: insights into specificity and potency," Bioorganic & Medicinal Chemistry Letters, 1999, 9:3335-3340.

Kojima et al., "Two-way cleavage of β-amyloid protein precursor by multicatalytic proteinase" Fed. Eur. Biochem. Soc. 304:57-60, Jun. 1992.

Koong et al. Hypoxia causes the activation of nuclear factor-kB through the phosphorylation of IκBα on tyrosine residuesl , Cancer Research, 54:1425-1430, Mar. 15, 1994.

Koong et al. Hypoxic activation of nuclear factor-κB is mediated by a Ras and Raf signaling pathway and does not involve MAP kinase (ERK1 or ERK2)1 , Cancer Research, 54:5273-5279, Oct. 15, 1994.

Krise et al. "A Novel Prodrug Approach for Tertiary Amines. Synthesis and Preliminary Evaluation of N-Phosphonooxymethyl Prodrugs", J. Med. Chem. 42:3094-3100, 1999.

Kumatori et al., "Abnormally high expression of proteasomes in human leukemic cells," Proc. Natl. Acad. Sci. USA, 1990, 87:7071-7075.

Lala et al., "Role of notric oxide in tymor progression: Lessons from experimental tumors," Cancer and Metastasis Reviews, 1998, 17:91-106.

Liang et al., "Synthesis of Cryptophycin 52 Using the Sharpless Asymmetric Dihydroxylation: Diol to Epoxide Transformation Optimized for a Base-Sensitive Substrate," J. Am. Chem. Soc., 2000, 65:3143-3147.

Loftsson et al., "Pharmaceutical Applications of Cyclodextrins. 1. Drug Solubilization and Stabalization," Journal of Pharmaceutical Sciences, American Pharmaceutical Association, 85(10):1017-1025 (1996).

McGraw-Hill Dictionary of Chemical Terms, 1990, p. 282.

Marx et al., "Reactivity-Selectivity in the Swern Oxidation of Alcohols Using Dimethyl Sulfoxide-Oxalyl Chloride," J. Org. Chem., 1984, 49:788-793.

Meng et al., "Eponemycin Exerts Its Antitumor Effect through the Inhibition of Proteasome Function," Cancer Research, 1999, 59:2798-2801.

Meng et al., "Epoxomicin, a potent and selective proteasome inhibitor, exhibits in vivo antiinflamatory activity," Proc. Natl. Acad. Sci. USA, 1999, 96:10403-10408.

Molecular biology and biotechnology a comprehensive desk reference: Edited by R A Meyers. pp. 658-664. VCH, Weinheim, Germany, 1995, DM89 ISBN 1-56081-925-1.

Molecular Probes, Inc. , "Introduction to Fluorescence techniques", invitrogen detection technologies, 11 pgs, Molecular Probes, Inc. (2007), Exhibit A to response filed with US Patent Office on Sep. 16, 2008 for U.S. Appl. No. 11/254,541 (now abandoned).

Morris, "Structural Aspects of Hydrates and Solvates in Polymorphism in Pharmaceutical Solids," Polymorphism in Pharmaceutical Solids, 1999, Ed. H.G. Nbrittain, Marcel Dekker, New York, pp. 125-181.

Myung et al., "Lack of Proteasome Active Site Allostery as Revealed by Subunit-Specific Inhibitors," Molecular Cell, 2001, 7(2):411-420.

Myung et al., "The Ubiquitin-Proteasome Pathway and Proteasome Inhibitors," Medicinal Research Reviews, 2001, 21(4):245-273.

Nemoto et al., "Catalytic Asymmetric Epoxidation of Enones Using La-BINOL-Triphenylarsine Oxide Complex: Structural Determination of the Asymmetric Catalyst," J. Am. Chem. Soc., 2001, 123:2725-2732.

Oishi et al., "Diastereoselective synthesis of new psi '(E)-CH=CMel- and psi '(Z)-CH=CMel-type alkene dipeptide isosteres by organocopper reagents and application to conformationally restricted cyclic RGD peptidomimetics," J. Org. Chem., 2002, 67:6162-6173.

Overkleeft et al. "Solid phase synthesis of peptide vinyl sulfone and peptide expoxyketone proteasome inhibitors", Tetrahedron Letters, 41(32), 6005-6009, 2000.

Palombella et al., "The Ubiquitin-Proteasome Pathway is Required for Processing the NF-.kappa.B1 Precursor Protein and the Activation of NF-.kappa.B," Cell, 1994, 78:773-785.

Paugam et al., "Characterization and role of protozoan parasite proteasomes," Trends Parasitol., 2003, 19:55-59.

Pye et al. "Proteasome inhibition ablates activation of NF-κB in myocardial reperfusion and reduces reperfusion of injury", Am. J. Physiol. Heart Circ. Physiol 284:H919-H926, 2003.

Qureshi et al., "The Proteasome as a Lipopolysaccharide-Binding Protein in Macrophages: Differential Effects of Proteasome Inhibition on Lipopolysaccharide-Induced Signaling Events," J. Immunology, 2003, 171:1515-1525.

Reidlinger et al. "Catalytic Properties of 26 S and 20 S Proteasomes and Radiolabling of MB 1, LMP7, and C7 Subunits Associated with Trypsin-like and Chymotrypsin-like Activities", J. of Biol Chem. 272(40), 24899-24905, May 27, 1997.

Safadi et al. "Phosphoryloxymet hyl Carbarnates and Carbonates-Novel Water-Soluble Prodrugs for Amines and Hindered Alcohols", Pharmaceutical Research 10(9), 1350-1355, Mar. 2, 1993.

Shao et al., "A New Asymmetric Synthesis of .alpha.-Methylcysteines via Chiral Aziridines," J. Org. Chem., 1995, 60:790-791.

Sharpless et al., "High Stereo- and Regioselectivities in the Transition Metal Catalyzed Epoxidations of Olefinic Alcohols by tert-Butyl Hydroperoxide," J. Am. Chem. Soc., 1973, 95:6136-6137.

Simsek et al. "Hepatitis B Virus Large and Middle Glycoproteins are Degraded by a Proteasome Pathway in Glucosidase-Inhibited Cells but Not in Cells with Functional Glucosidase Enzyme", J. Virol. 79(20), 12914-12920, Oct. 2005.

Sin et al., "Total synthesis of the potent proteasome inhibitor epoxomicin: a useful tool for understanding proteasome biology," Bioorganic & Medicinal Chemistry Letters, 1999, 9:2283-2288.

Spaltenstein et al., "Design and Synthesis of Novel Protease Inhibitors. Tripeptide .alpha.',.beta.'-Epoxyketones as Nanomolar Inactivators of the Proteasome," Tetrahedron Letters, 1996, 37:1343-1346.

Stein et al., "Kinetic Characterization of the Chymotryptic Activity of the 20S Proteasome," Biochemistry, 1996, 35:3899-3908.

Strickley, Robert G., "Solubilizing Excipients in Oral and Injectable Formulations," Pharmaceutical Research, 21(2):201-230 (2004).

Szalay et al. "Ongoing coxsackievirus myocarditis is associated with increased formation and activity of myocardial immunoproteaseomes", Am. J. Pathol. 168(5), 1542-1552, May 2006.

Terato et al. "Induction of arthritis with monoclonal antibodies to collagen1" J. Immunol, 148(7), 2103-2108, Apr. 1, 1992.

Thanos et al., "NF-.kappa.B: A Lesson in Family Values," Cell, 1995, 80:529-532.

Thompson., "Cyclodextrins-enabling excipients: their present and future use in pharmaceuticals," Critical Reviews in Therapeutic Drug Carrier Systems, 14(1):1-104 (1997).

Tong, Wei-Qin (Tony), "Applications of Complexation in the Formulation of Insoluble Compounds," R. Liu, Ed., pp. 111-139 (2000).

Traenckner et al., "A proteasome inhibitor prevents activation of NF-.kappa.B and stabilizes a newly phosphorylated form of I.kappa.B-.alpha. that is still bound to NF-.kappa.B," EMBO J., 1994, 13:5433-5441.

Tu et al., "An Efficient Assymettric Epoxidation Method for trans-Olefins Mediated by a Fructose-Derived Ketone," J. Am. Chem. Soc., 1996, 118:9806-9807.

Vogel's textbook of practical organic chemistry, 5th Ed. See p. 135, "2.20 Recrystallisation Techniques" and p. 141, 2nd paragraph onwards, 1996.

Voskoglou-Nomikos, "Clinical Predictive Value of the in Vitro Cell Line, Human Xenograft, and Mouse Allograft Preclinical Cancer Models," Clin Cancer Res., 2003, 9(11):4227-4239.

Wang et al., "A New Type of Ketone Catalyst for Asymmetric Epoxidation," J. Org. Chem., 1997, 62:8622-8623.

Wipf et al., "Methyl- and (Trifluoromethyl)alkene Peptide Isosteres: Synthesis and Evaluation of Their Potential as .beta.-Turn Promoters and Peptide Mimetics," J. Org. Chem., 1998, 63:6088-6089.

Xu et al. "Mutations in the tumor suppressors Smad2 and Smad4 inactivate transforming growth factor β signaling by targeting Smads to the ubiquitin-proteasome pathway", PNAS 97(9), 4820-4825, Apr. 25, 2000.

Yu et al. "The Ubiquitin-Proteasome System Facilitates the Transfer of Murine Coronavirus from Endosome to Cytoplasm during Virus Entry", J. Virol. 79(1), 644-648, Jan. 2005.

Zhou et al., "Design and Synthesis of an Orally Bioavailable and Selectrive Peptide Epoxyketone Proteasome Inhibitor (PR-047)," J. Med. Chem., 2009, 52 (9):3028-3038.

Elliott et al., "The Proteasome A New Target for Novel Drug Therapies," Am J Clin Pathol., 2001, 116:637-646.

Le Blanc et al., "Growth in Vivo and Prolongs Survival in a Murine Model Proteasome Inhibitor PS-341 Inhibits Human Myeloma Cell," Cancer Research, 2002, 62:4996-5000, Published online Sep. 1, 2002.

Adams, "The development of proteasome inhibitors as anticancer drugs," Cancer Cell, May 2003, 5:417-421.

Adams, Cancer Drug Discovery and Development, Protease Inhibitors in Cancer Therapy, 2004. Human Press, Chapter 20, Phase I trials, pp. 271-282.

Rossi et al., "Proteasome inhibitors in cancer therapy: death by indigestion," Cell Death and Differentiation, 2005, as:1255-1257.

Roccaro et al., "Selective inhibition of chymotrypsin-like activity of the immunoproteasome and constitutive proteasome in Waldenström macroglobulimia," Blood, 2010, 115:4051-4060.

Orlowski and Kuhn, "Proteasome Inhibitors in Cancer Therapy: Lessons from the First Decade," Clin. Canc. Res., 2008, 14:1649-165.

Center for Drug Evaluation and Research, Application No. 21-602, Medical Review, Clinical NDA Review, "NDA 21-602 VELVADE™ (bortexomib) for injection," Clinical Review, 1-47, 2003.

Center for Drug Evaluation and Research, Application No. 21-602, Medical Review, Clinical NDA Review, "NDA 21-602 VELCADE™ (bortexomib) for injection," Clinical Review, 81-125, 2003.

Center for Drug Evaluation and Research, Application No. 21-602, Medical Review, Clinical NDA Review, "NDAa 21-602 VELCADE™ (bortexomib) for injection," Clinical Review, 1-34, 2003.

Orlowski et al., "Phase I Trial of the Proteasome Inhibitor PS-341 in Patients With Refractory Hematologic Malignancies," Journal of Clinical Oncology, 2002, 20(22):4420-4427.

European Search Report, EP 08 16 4241, completed Jan. 22, 2009, 5 pages.

International Search Report and Written Opinion for corresponding PCT Application No. PCT/US2005/016335, mailed Jan. 2, 2006, 17 pgs.

International Preliminary Report on Patentability for corresponding PCT Application No. PCT/US2005/016335, issued Nov. 14, 2006, 11 pgs.

International Search Report and Written Opinion for corresponding PCT Application No. PCT/US2005/012740, mailed Jan. 9, 2006, 16 pgs.

International Preliminary Report on Patentability for corresponding PCT Application No. PCT/US2005/012740, issued Oct. 19, 2006, 11 pgs.

Authorized Officer M. Kollmannsberger, International Search Report and Written Opinion for PCT/US2007/014427, mailed Dec. 3, 2007, 12 pages.

Authorized Officer M. Kollmannsberger, International Preliminary Report on Patentability PCT/US2007/014427, issued Dec. 22, 2008, 8 pages.

European Search Report, EP 09 00 6228, completed Aug. 25, 2009, 7 pages.

Authorized Officer A. Schleifenbaum, International Search Report and Written Opinion of the International Searching Authority for PCT/US2008/005997, mailed Nov. 7, 2008, 8 pages.

Authorized Officer Philippe Becamel, International Preliminary Report on Patentability for PCT/US2008/005997, issued Nov. 10, 2009, 7 pages.

Authorized Officer Grant McNeice, International Search Report for PCT/US2009/061498, mailed Dec. 10, 2009, 5 pages.

Authorized Officer Sonya James, International Search Report and Written Opinion of the International Searching Authority for PCT/US2006/043503, mailed Feb. 19, 2007, 17 pages.

Authorized Officer Dorothée Mülhausen, International Search Report and Written Opinion of the International Searching Authority for PCT/US2006/043503, mailed Feb. 19, 2007, 17 pages.

Authorized Officer Marc Kloth, International Search Report and Written Opinion of the Internatinal Searching Authority for PCT/US2010/028126, mailed Jun. 9, 2010, 13 pages.

Partial International Search Report for PCT/US2008/011443, dated Dec. 9, 2008, 6 pages.

Authorized Officer M. Groenendijk, International Search Report and Written Opinion of the International Searching Authority for PCT/US2005/028246, mailed Jan. 19, 2006, 11 pages.

Authorized Officer Yoshiko Kuwahara, International Preliminary Report on Patentability for PCT/US2005/028246, issued Feb. 6, 2007, 8 pages.

Authorized Officer D. Grassi, International Search Report and Written Opinion of the International Searching Authority for PCT/US2005/017000, mailed Feb. 3, 2006, 12 pages.

Authorized Beate Giffo-Schmitt, International Preliminary Report on Patentability for PCT/US2005/017000, issued Nov. 21, 2006, 12 pages.

Authorized Officer M. Groenendijk, International Search Report and Written Opinion of the International Searching Authority for PCT/US2005/037966, mailed Jan. 24, 2006, 17 pages.

Authorized Officer Dorothée Mülhausen, International Preliminary Report on Patentability for PCT/US2005/037966, issued Apr. 24, 2007, 12 pages.

Authorized Officer M. Groenendijk, International Search Report and Written Opinion of the International Searching Authority for PCT/US2005/044451, mailed May 2, 2006, 12 pages.

Authorized Officer Philippe Becamel, International Preliminary Report on Patentability for PCT/US2005/044451, issued Jun. 13, 2007, 8 pages.

Authorized Officer Sonya James, International Search Report and Written Opinion of the International Searching Authority for PCT/US2008/011443, mailed Mar. 25, 2009, 16 pages.

Authorized Officer Athina Nickitas-Etienne, International Preliminary Report on Patentability for PCT/US2008/011443, issued Apr. 7, 2010, 12 pages.

Wilson et al., "Novel disease targets and management approaches for diffuse large B-cell lymphoma" Informa Healthcare, 51(1):1, 2010.

Cecil text book of medicine, vol. 2, $20^{th}$ Ed., W.B. Saunders Company pp. 2050-2057, 1996.

Cecil text book of medicine, vol. 2, $20^{th}$ Ed., W.B. Saunders Company pp. 1992-1996, 1996.

CNN.com "FDA mulls drug to slow late-stage Alzheimer's" Retrieved from http://www.cnn.com./2003/HEALTH/conditions/09/24/alzheimers.drug.ap/index.html Sep. 24, 2003.

Huff, "HIV Protease: A Novel Chemotherapeutic Target for AIDS", Journal of Medicinal Chemistry, 34(8):2305-2314, 1991.

Mandel et al. "Neuroprotective Strategies in Parkinson's Disease" CNS Drugs 17(10):729-762, 2003.

Kuhn et al. "Potent activity of carfilzomib, a novel, irreversible inhibitor of the ubiquitin-proteasome pathway, against preclinical models of multiple myeloma" bloodjournal.hematologylibrary.org Jun. 25, 2007 (11 pages).

_US 8,324,174 B2_

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Leu Val Tyr
  1

<210> SEQ ID NO 2
<211> LENGTH: 10
<212> TYPE: PRT
<213> ORGANISM: Rattus sp.
<220> FEATURE:
<221> NAME/KEY: MOD_RES
<222> LOCATION: (1)
<223> OTHER INFORMATION: Variable amino acid
<220> FEATURE:
<221> NAME/KEY: MOD_RES
<222> LOCATION: (6)
<223> OTHER INFORMATION: Variable amino acid

<400> SEQUENCE: 2

Xaa Gln Asn Pro Met Xaa Thr Gly Thr Ser
  1               5                  10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ala Ala Leu Gly Asn Ile Ser Glu Asn
  1               5                  10
```

COMPOUNDS FOR ENZYME INHIBITION

CLAIM OF PRIORITY

This application is a continuation of U.S. ("U.S.") application Ser. No. 11/578,626, which has a mail date of Oct. 16, 2006 and a 35 U.S.C. §371(c) date of Aug. 10, 2007 and is the U.S. National Stage of International Application No. PCT/US2005/012740, filed on Apr. 14, 2005, which in turn claims the benefit of U.S. Provisional Application No. 60/562,340, filed on Apr. 15, 2004; U.S. Provisional Application No. 60/569,096, filed on May 7, 2004; U.S. Provisional Application No. 60/599,401, filed on Aug. 6, 2004; U.S. Provisional Application No. 60/610,001, filed on Sep. 14, 2004; U.S. Provisional Application No. 60/610,002, filed on Sep. 14, 2004; U.S. Provisional Application No. 60/610,159, filed on Sep. 14, 2004; and U.S. Provisional Application No. 60/620,573, filed on Oct. 20, 2004; each of these prior filed applications is incorporated herein by reference in its entirety.

TECHNICAL FIELD

This invention relates to compounds and methods for enzyme inhibition. In particular, the invention relates to therapeutic methods based on enzyme inhibition.

BACKGROUND OF THE INVENTION

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multicatalytic protease, which cleaves proteins into short peptides through the action of its three major proteolytic activities. While having a general function in intracellular protein turnover, proteasome-mediated degradation also plays a key role in many processes such as major histocompatibility complex (MHC) class I presentation, apoptosis, cell division, and NF-κB activation.

The 20S proteasome is a 700 kDa cylindrical-shaped multicatalytic protease complex comprised of 28 subunits organized into four rings that plays important roles in cell growth regulation, major histocompatibility complex class I presentation, apoptosis, antigen processing, NF-κB activation, and transduction of pro-inflammatory signals. In yeast and other eukaryotes, 7 different α subunits form the outer rings and 7 different β subunits comprise the inner rings. The α subunits serve as binding sites for the 19S (PA700) and 11S (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome. Cleavage of amino-terminal prosequences of β subunits during particle formation expose amino-terminal threonine residues, which serve as the catalytic nucleophiles. The subunits responsible for catalytic activity in proteasome thus possess an amino terminal nucleophilic residue, and these subunits belong to the family of N-terminal nucleophile (Ntn) hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three γ-interferon-inducible β subunits (LMP7, LMP2 and MECL1), which replace their normal counterparts, X, Y and Z respectively, thus altering the catalytic activities of the proteasome. Through the use of different peptide substrates, three major proteolytic activities have been defined for the eukaryote 20S proteasome: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. The major proteasome proteolytic activities appear to be contributed by different catalytic sites, since inhibitors, point mutations in β subunits and the exchange of γ interferon-inducing β subunits alter these activities to various degrees.

There are several examples of small molecules which have been used to inhibit proteasome activity; however, these compounds generally lack the specificity, stability, or potency necessary to explore and exploit the roles of the proteasome at the cellular and molecular level. Therefore, the synthesis of small molecule inhibitor(s) with increased site specificity, improved stability and solubility, and increased potency are needed to allow the exploration of the roles of the proteasome at the cellular and molecular level.

SUMMARY OF THE INVENTION

The invention relates to analogs and prodrugs of classes of molecules known as peptide α',β'-epoxides and peptide α',β'-aziridines. The parent molecules are understood to bind efficiently, irreversibly and selectively to N-terminal nucleophile (Ntn) hydrolases, and can specifically inhibit particular activities of enzymes having multiple catalytic activity.

Once thought merely to dispose of denatured and misfolded proteins, the proteasome is now recognized as constituting proteolytic machinery that regulates the levels of diverse intracellular proteins through their degradation in a signal-dependent manner. Hence, there is great interest in identifying reagents that can specifically perturb the activities of the proteasome and other Ntn hydrolases and thereby be used as probes to study the role of these enzymes in biological processes. Analogs and prodrugs for compounds that target the Ntn hydrolases are herein described, synthesized, and investigated. Peptide epoxides and peptide aziridines that can potently, selectively, and irreversibly inhibit particular proteasome activities are disclosed and claimed.

Unlike several other peptide-based inhibitors, the peptide epoxides and peptide aziridines described herein are not expected to substantially inhibit non-proteasomal proteases such as trypsin, chymotrypsin, cathepsin B, papain, and calpain at concentrations up to 50 μM. At higher concentrations, inhibition may be observed, but would be expected to be competitive and not irreversible, if the inhibitor merely competes with the substrate. The novel peptide epoxides and peptide aziridines are also expected to inhibit NF-κB activation and to stabilize p53 levels in cell culture. Moreover, these compounds would be expected to have anti-inflammatory activity. Thus, these compounds can be unique molecular probes, which have the versatility to explore Ntn enzyme function in normal biological and pathological processes.

In one aspect, the invention provides inhibitor analogs and prodrugs comprising a heteroatom-containing three-membered ring. These inhibitors can inhibit catalytic activity of N-terminal nucleophile hydrolase enzymes (for example, the 20S proteasome, or the 26S proteasome) when said inhibitor is present at concentrations below about 50 μM. Regarding the 20S proteasome, particular hydrolase inhibitors inhibit chymotrypsin-like activity of the 20S proteasome when the inhibitor is present at concentrations below about 5 μM, and does not inhibit trypsin-like activity or PGPH activity of the 20S proteasome when present at concentrations below about 5 μM. The hydrolase inhibitor may be, for example, a peptide α',β'-epoxy ketone or α',β'-aziridine ketone, and the peptide may be a tetrapeptide. The tetrapeptide may include branched or unbranched side chains such as hydrogen, $C_{1-6}$alkyl, $C_{1-6}$hydroxyalkyl, $C_{1-6}$alkoxyalkyl, aryl, $C_{1-6}$aralkyl, $C_{1-6}$alkylamide, $C_{1-6}$alkylamine, $C_{1-6}$-carboxylic acid, $C_{1-6}$-carboxyl ester, $C_{1-6}$alkylthiol, or $C_{1-6}$alkylthioether, for example isobutyl, 1-naphthyl, phenylmethyl, and 2-phenylethyl. The α'-carbon of the α',β'-epoxy ketone or α',β'-aziridine ketone may be a chiral carbon atom, such as an (R) or β configured carbon, as these are defined herein.

In another aspect, the invention provides pharmaceutical compositions, including a pharmaceutically acceptable carrier and a pharmaceutically effective amount of the hydrolase inhibitor analog or prodrug, which ameliorates the effects of neurodegenerative disease (such as Alzheimer's disease), muscle-wasting diseases, cancer, chronic infectious diseases, fever, muscle disuse, denervation, nerve injury, fasting, and immune-related conditions, among others.

In another aspect, the invention provides anti-inflammatory compositions.

In another aspect, the invention provides methods for the following: inhibiting or reducing HIV infection in a subject; affecting the level of viral gene expression in a subject; altering the variety of antigenic peptides produced by the proteasome in an organism; determining whether a cellular, developmental, or physiological process or output in an organism is regulated by the proteolytic activity of a particular Ntn hydrolase; treating Alzheimer's disease in a subject; reducing the rate of muscle protein degradation in a cell; reducing the rate of intracellular protein degradation in a cell; reducing the rate of p53 protein degradation in a cell; inhibiting the growth of p53-related cancers in a subject; inhibiting antigen presentation in a cell; suppressing the immune system of a subject; inhibiting IκB-α degradation in an organism; reducing the content of NF-κB in a cell, muscle, organ or subject; affecting cyclin-dependent eukaryotic cell cycles; treating proliferative disease in a subject; affecting proteasome-dependent regulation of oncoproteins in a cell; treating cancer growth in a subject; treating p53-related apoptosis in a subject; and screening proteins processed by N-terminal nucleophile hydrolases in a cell. Each of these methods involves administering or contacting an effective amount of a composition comprising the hydrolase inhibitors disclosed herein, to a subject, a cell, a tissue, an organ, or an organism.

Other features and advantages of the invention will be apparent from the following detailed description, and from the claims.

DETAILED DESCRIPTION OF THE INVENTION

The invention involves compounds useful as enzyme inhibitors. These compounds are generally useful to inhibit enzymes having a nucleophilic group at the N-terminus. For example, activities of enzymes or enzyme subunits having N-terminal amino acids with nucleophiles in their side chains, such as threonine, serine, or cysteine can be successfully inhibited by the enzyme inhibitors described herein. Activities of enzymes or enzyme subunits having non-amino acid nucleophilic groups at their N-termini, such as, for example, protecting groups or carbohydrates, can also be successfully inhibited by the enzyme inhibitors described herein.

While not bound by any particular theory of operation, it is believed that such N-terminal nucleophiles of Ntn form covalent adducts with the epoxide functional group of the enzyme inhibitors described herein. For example, in the β5/Pre2 subunit of 20S proteasome, the N-terminal threonine is believed to irreversibly form a morpholino or piperazino adduct upon reaction with a peptide epoxide or aziridine such as those described below. Such adduct formation would involve ring-opening cleavage of the epoxide or aziridine.

In embodiments including such groups bonded to α' carbons, the stereochemistry of the α'-carbon (that carbon forming a part of the epoxide or aziridine ring) can be (R) or (S). The invention is based, in part, on the structure-function information disclosed herein, which suggests the following preferred stereochemical relationships. Note that a preferred compound may have a number of stereocenters having the indicated up-down (or β-α, where β as drawn herein is above the plane of the page) or (R)-(S) relationship (that is, it is not required that every stereocenter in the compound conform to the preferences stated). In some preferred embodiments, the stereochemistry of the α' carbon is (R), that is, the X atom is β, or above the plane of the molecule.

Regarding the stereochemistry, the Cahn-Ingold-Prelog rules for determining absolute stereochemistry are followed. These rules are described, for example, in *Organic Chemistry*, Fox and Whitesell; Jones and Bartlett Publishers, Boston, Mass. (1994); Section 5-6, pp 177-178, which section is hereby incorporated by reference. Peptides can have a repeating backbone structure with side chains extending from the backbone units. Generally, each backbone unit has a side chain associated with it, although in some cases, the side chain is a hydrogen atom. In other embodiments, not every backbone unit has an associated side chain. Peptides useful in peptide epoxides or peptide aziridines have two or more backbone units. In some embodiments useful for inhibiting chymotrypsin-like (CT-L) activity of the proteasome, between four and eight backbone units are present, and in some preferred embodiments for CT-L inhibition, between four and six backbone units are present.

The side chains extending from the backbone units can include natural aliphatic or aromatic amino acid side chains, such as hydrogen (glycine), methyl (alanine), isopropyl (valine), sec-butyl (isoleucine), isobutyl (leucine), phenylmethyl (phenylalanine), and the side chain constituting the amino acid proline. The side chains can also be other branched or unbranched aliphatic or aromatic groups such as ethyl, n-propyl, n-butyl, t-butyl, and aryl substituted derivatives such as 1-phenylethyl, 2-phenylethyl, (1-naphthyl)methyl, (2-naphthyl)methyl, 1-(1-naphthyl)ethyl, 1-(2-naphthyl)ethyl, 2-(1-naphthyl)ethyl, 2-(2-naphthyl)ethyl, and similar compounds. The aryl groups can be further substituted with branched or unbranched $C_{1-6}$alkyl groups, or substituted alkyl groups, acetyl and the like, or further aryl groups, or substituted aryl groups, such as benzoyl and the like. Heteroaryl groups can also be used as side chain substituents. Heteroaryl groups include nitrogen-, oxygen-, and sulfur-containing aryl groups such as thienyl, benzothienyl, naphthothienyl, thianthrenyl, furyl, pyranyl, isobenzofuranyl, chromenyl, pyrrolyl, imidazolyl, pyrazolyl, pyridyl, pyrazinyl, indolyl, purinyl, quinolyl, and the like.

In some embodiments, polar or charged residues can be introduced into the peptide epoxides or peptide aziridines. For example, naturally occurring amino acids such as hydroxy-containing (Thr, Tyr, Ser) or sulfur-containing (Met, Cys) can be introduced, as well as non-essential amino acids, for example, taurine, carnitine, citrulline, cystine, ornithine, norleucine and others. Non-naturally occurring side chain substituents with charged or polar moieties can also be included, such as, for example, $C_{1-6}$alkyl chains or $C_{6-12}$aryl groups with one or more hydroxy, short chain alkoxy, sulfide, thio, carboxyl, ester, phospho, amido or amino groups, or such substituents substituted with one or more halogen atoms. In some preferred embodiments, there is at least one aryl group present in a side chain of the peptide moiety.

In some embodiments, the backbone units are amide units [—NH—CHR—C(=O)—], in which R is the side chain. Such a designation does not exclude the naturally occurring amino acid proline, or other non-naturally occurring cyclic secondary amino acids, which will be recognized by those of skill in the art.

In other embodiments, the backbone units are N-alkylated amide units (for example, N-methyl and the like), olefinic analogs (in which one or more amide bonds are replaced by olefinic bonds), tetrazole analogs (in which a tetrazole ring imposes a cis-configuration on the backbone), or combinations of such backbone linkages. In still other embodiments, the amino acid α-carbon is modified by α-alkyl substitution, for example, aminoisobutyric acid. In some further embodiments, side chains are locally modified, for example, by $\Delta^E$ or $\Delta^z$ dehydro modification, in which a double bond is present between the α and β atoms of the side chain, or for example by $\Delta^E$ or $\Delta^z$ cyclopropyl modification, in which a cyclopropyl group is present between the α and β atoms of the side chain. In still further embodiments employing amino acid groups, D-amino acids can be used. Further embodiments can include side chain-to-backbone cyclization, disulfide bond formation, lactam formation, azo linkage, and other modifications discussed in "Peptides and Mimics, Design of Conformationally Constrained" by Hruby and Boteju, in "Molecular Biology and Biotechnology: A Comprehensive Desk Reference", ed. Robert A. Meyers, VCH Publishers (1995), pp. 658-664, which is hereby incorporated by reference.

In certain embodiments, the subject compounds are analogs or prodrugs of the compounds disclosed in U.S. application Ser. No. 09/569,748, the contents of which are hereby incorporated by reference in their entirety. Suitable enzyme inhibitor analogs or prodrugs may have a structure of formula (I) or a pharmaceutically acceptable salt thereof,

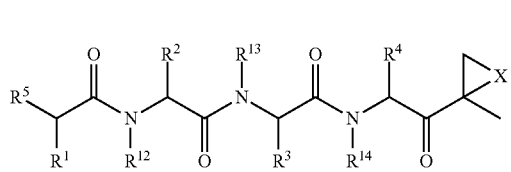

(I)

wherein each A is independently selected from C=O, C=S, and $SO_2$, preferably C=O; or A is optionally a covalent bond when adjacent to an occurrence of Z;

L is absent or is selected from C=O, C=S, and $SO_2$, preferably L is absent or C=O;

M is absent or is $C_{1-12}$alkyl, preferably $C_{1-8}$alkyl;

Q is absent or is selected from O, NH, and N—$C_{1-6}$alkyl, preferably Q is absent, O, or NH, most preferably Q is absent or O;

X is selected from O, NH, and N—$C_{1-6}$alkyl, preferably O;

Y is absent or is selected from O, NH, N—$C_{1-6}$alkyl, S, SO, $SO_2$, $CHR^{10}$, and $CHCO_2R^{10}$;

each Z is independently selected from O, S, NH, and N—$C_{1-6}$alkyl, preferably O; or Z is optionally a covalent bond when adjacent to an occurrence of A;

$R^1$, $R^2$, $R^3$, and $R^4$ are each independently selected from $C_{1-6}$alkyl, $C_{1-6}$hydroxyalkyl, $C_{1-6}$alkoxyalkyl, aryl, and $C_{1-6}$aralkyl, any of which is optionally substituted with one or more of amide, amine, carboxylic acid (or a salt thereof), ester (including $C_{1-5}$ alkyl ester and aryl ester), thiol, or thioether substituents;

$R^5$ is $N(R^6)LQR^7$;

$R^6$, $R^{12}$, $R^{13}$, and $R^{14}$ are independently selected from hydrogen, OH, $C_{1-6}$alkyl, and a group of formula IV; preferably, $R^6$ is selected from hydrogen, OH, and $C_{1-6}$alkyl, and $R^{12}$, $R^{13}$, and $R^{14}$ are independently selected from hydrogen and $C_{1-6}$alkyl, preferably hydrogen;

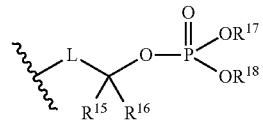

IV $R^7$ is selected from hydrogen, $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^8ZAZ$-$C_{1-8}$alkyl-, $R^{11}Z$—$C_{1-8}$alkyl-, $(R^8O)(R^9O)P(=O)O$—$C_{1-8}$alkyl-$ZAZ$-$C_{1-8}$alkyl-, $R^8ZAZ$-$C_{1-8}$alkyl-$ZAZ$-$C_{1-8}$alkyl-, heterocyclylMZAZ-$C_{1-8}$alkyl-, $(R^8O)(R^9O)P(=O)O$—$C_{1-8}$alkyl-, $(R^{10})_2N$—$C_{1-12}$alkyl-, $(R^{10})_3N^+$—$C_{1-12}$alkyl-, heterocyclylM-, carbocyclylM-, $R^{11}SO_2C_{1-8}$alkyl-, and $R^{11}SO_2NH$; preferably $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^8ZA$-$C_{1-8}$alkyl-, $R^{11}Z$—$C_{1-8}$alkyl-, $(R^8O)(R^9O)P(=O)O$—$C_{1-8}$alkyl-$ZAZ$-$C_{1-8}$alkyl-, $(R^8O)(R^9O)P(=O)O$—$C_{1-8}$alkyl-$Z$—$C_{1-8}$alkyl-, $R^8ZA$-$C_{1-8}$alkyl-$ZAZ$-$C_{1-8}$alkyl-, heterocyclylMZAZ-$C_{1-8}$alkyl-, $(R^8O)(R^9O)P(=O)O$—$C_{1-8}$alkyl-, $(R^{10})_2N$—$C_{1-8}$alkyl-, $(R^{10})_3N^+$—$C_{1-8}$alkyl-, heterocyclylM-, carbocyclylM-, $R^{11}SO_2C_{1-8}$alkyl-, and $R^{11}SO_2NH$, wherein each occurrence of Z and A is independently other than a covalent bond; or $R^6$ and $R^7$ together are $C_{1-6}$alkyl-Y—$C_{1-6}$alkyl, $C_{1-6}$alkyl-$ZAZ$-$C_{1-6}$alkyl, $ZAZ$-$C_{1-6}$alkyl-$ZAZ$-$C_{1-6}$alkyl, $ZAZ$-$C_{1-6}$ alkyl-$ZAZ$, or $C_{1-6}$alkyl-A, thereby forming a ring; preferably $C_{1-2}$alkyl-Y—$C_{1-2}$alkyl, $C_{1-2}$alkyl-$ZA$-$C_{1-2}$alkyl, A-$C_{1-2}$alkyl-$ZA$-$C_{1-2}$alkyl, A-$C_{1-3}$alkyl-A, or $C_{1-4}$alkyl-A, wherein each occurrence of Z and A is independently other than a covalent bond;

$R^8$ and $R^9$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^8$ and $R^9$ together are $C_{1-6}$alkyl, thereby forming a ring;

each $R^{10}$ is independently selected from hydrogen and $C_{1-6}$alkyl, preferably $C_{1-6}$alkyl; and $R^{11}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl, $R^{15}$ and $R^{16}$ are independently selected from hydrogen and $C_{1-6}$alkyl, or $R^{15}$ and $R^{16}$ together form a 3- to 6-membered carbocyclic or heterocyclic ring; and $R^{17}$ and $R^{18}$ are independently selected from hydrogen, a metal cation, $C_{1-6}$alkyl, and $C_{1-6}$aralkyl, or $R^{17}$ and $R^{18}$ together represent $C_{1-6}$alkyl, thereby forming a ring;

provided that when $R^6$, $R^{12}$, $R^{13}$, and $R^{14}$ are H or $CH_3$, and Q is absent, $LR^7$ is not hydrogen, unsubstituted $C_{1-6}$alkylC=O, a further chain of amino acids, t-butoxycarbonyl (Boc), benzoyl (Bz), fluoren-9-ylmethoxycarbonyl (Fmoc), triphenylmethyl(trityl), benzyloxycarbonyl (Cbz), trichloroethoxycarbonyl (Troc); or substituted or unsubstituted aryl or heteroaryl; and in any occurrence of the sequence ZAZ, at least one member of the sequence must be other than a covalent bond.

In certain embodiments, when $R^6$ is H, L is C=O, and Q is absent, $R^7$ is not hydrogen, $C_{1-6}$alkyl, or substituted or unsubstituted aryl or heteroaryl. In certain embodiments, when $R^6$ is H and Q is absent, $R^7$ is not a protecting group such as those described in Greene, T. W. and Wuts, P. G. M., "Protective Groups in Organic Synthesis", John Wiley & Sons, 1999 or Kocieński, P. J., "Protecting Groups", Georg Thieme Verlag, 1994.

In some embodiments, $R^1$, $R^2$, $R^3$, and $R^4$ are selected from $C_{1-6}$alkyl or $C_{1-6}$aralkyl. In preferred embodiments, $R^2$ and $R^4$ are $C_{1-6}$alkyl and $R^1$ and $R^3$ are $C_{1-6}$aralkyl. In the most preferred embodiment, $R^2$ and $R^4$ are isobutyl, $R^1$ is 2-phenylethyl, and $R^3$ is phenylmethyl.

In certain embodiments, L and Q are absent and $R^7$ is selected from $C_{1-6}$alkyl, $C_{1-6}$alkenyl, $C_{1-6}$alkynyl, $C_{1-6}$aralkyl, and $C_{1-6}$heteroaralkyl. In certain such embodiments, $R^6$ is $C_{1-6}$alkyl and $R^7$ is selected from butyl, allyl, propargyl, phenylmethyl, 2-pyridyl, 3-pyridyl, and 4-pyridyl.

In other embodiments, L is $SO_2$, Q is absent, and $R^7$ is selected from $C_{1-6}$alkyl and aryl. In certain such embodiments, $R^7$ is selected from methyl and phenyl.

In certain embodiments, L is C=O and $R^7$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^8ZA$-$C_{1-8}$alkyl-, $R^{11}Z$—$C_{1-8}$alkyl-, $(R^8O)(R^9O)P(=O)O$—$C_{1-8}$alkyl-, $(R^8O)(R^9O)P(=O)O$—$C_{1-8}$alkyl-ZAZ-$C_{1-8}$alkyl-, $(R^8O)(R^9O)P(=O)O$—$C_{1-8}$alkyl-Z—$C_{1-8}$alkyl-, $R^8ZA$-$C_{1-8}$alkyl-ZAZ-$C_{1-8}$alkyl-, heterocyclylMZAZ-$C_{1-8}$alkyl-, $(R^{10})_2N$—$C_{1-8}$ alkyl-, $(R^{10})_3N^+$—$C_{1-8}$alkyl-, heterocyclylM-, carbocyclylM-, $R^{11}SO_2C_{1-8}$alkyl-, and $R^{11}SO_2NH$—, wherein each occurrence of Z and A is independently other than a covalent bond.

In certain embodiments, L is C=O, Q is absent, and $R^7$ is H.

In certain embodiments, $R^6$ is $C_{1-6}$alkyl, $R^7$ is $C_{1-6}$alkyl, Q is absent, and L is C=O. In certain such embodiments, $R^7$ is ethyl, isopropyl, 2,2,2-trifluoroethyl, or 2-(methylsulfonyl)ethyl.

In other embodiments, L is C=O, Q is absent, and $R^7$ is $C_{1-6}$aralkyl. In certain such embodiments, $R^7$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^6$ is $C_{1-6}$alkyl, and $R^7$ is aryl. In certain such embodiments, $R^7$ is substituted or unsubstituted phenyl.

In certain embodiments, L is C=O, Q is absent or O, n is 0 or 1, and $R^7$ is —$(CH_2)_n$carbocyclyl. In certain such embodiments, $R^7$ is cyclopropyl or cyclohexyl.

In certain embodiments, L and A are C=O, Q is absent, Z is O, n is an integer from 1 to 8 (preferably 1), and $R^7$ is selected from $R^8ZA$-$C_{1-8}$alkyl-, $R^{11}Z$—$C_{1-8}$alkyl-, $R^8ZA$-$C_{1-8}$alkyl-ZAZ-$C_{1-8}$alkyl-, $(R^8O)(R^9O)P(=O)O$—$C_{1-8}$alkyl-ZAZ-$C_{1-8}$alkyl-, $(R^8O)(R^9O)P(=O)O$—$C_{1-8}$alkyl-Z—$C_{1-8}$alkyl-, and heterocyclylMZAZ-$C_{1-8}$alkyl-, wherein each occurrence of A is independently other than a covalent bond. In certain such embodiments, $R^7$ is heterocyclylM-ZAZ-$C_{1-8}$alkyl- where heterocyclyl is substituted or unsubstituted oxodioxolenyl or $N(R^{12})(R^{13})$, wherein $R^{12}$ and $R^{13}$ together are $C_{1-6}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, n is an integer from 1 to 8, and $R^7$ is selected from $(R^8O)(R^9O)P(=O)O$—$C_{1-8}$alkyl-, $(R^{10})_2NC_{1-8}$alkyl, $(R^{10})_3N^+(CH_2)_n$—, and heterocyclyl-M-. In certain such embodiments, $R^7$ is —$C_{1-8}$alkylN$(R^{10})_2$ or —$C_{1-8}$alkylN$^+(R^{10})_3$, where $R^{10}$ is $C_{1-6}$alkyl. In certain other such embodiments, $R^7$ is heterocyclylM-, where heterocyclyl is selected from morpholino, piperidino, piperazino, and pyrrolidino.

In certain embodiments, L is C=O, $R^6$ is $C_{1-6}$alkyl, Q is selected from O and NH and $R^7$ is selected from $C_{1-6}$alkyl, cycloalkyl-M, $C_{1-6}$aralkyl, and $C_{1-6}$heteroaralkyl. In other embodiments, L is C=O, $R^6$ is $C_{1-6}$alkyl, Q is selected from O and NH, and $R^7$ is $C_{1-6}$alkyl, where $C_{1-6}$alkyl is selected from methyl, ethyl, and isopropyl. In further embodiments, L is C=O, $R^6$ is $C_{1-6}$alkyl, Q is selected from O and NH and $R^7$ is $C_{1-6}$aralkyl, where aralkyl is phenylmethyl. In other embodiments, L is C=O, $R^6$ is $C_{1-6}$alkyl, Q is selected from O and NH, and $R^7$ is $C_{1-6}$heteroaralkyl, where heteroaralkyl is (4-pyridyl)methyl.

In certain embodiments, L is absent or is C=O, and $R^6$ and $R^7$ together are $C_{1-6}$alkyl-Y—$C_{1-6}$alkyl, $C_{1-6}$alkyl-ZA-$C_{1-6}$alkyl, or $C_{1-6}$alkyl-A, wherein each occurrence of Z and A is independently other than a covalent bond, thereby forming a ring. In certain preferred embodiments, L is C=O, Q and Y are absent, and $R^6$ and $R^7$ together are $C_{1-3}$alkyl-Y—$C_{1-3}$alkyl. In another preferred embodiment, L and Q are absent, and $R^6$ and $R^7$ together are $C_{1-3}$alkyl-Y—$C_{1-3}$alkyl. In another preferred embodiment, L is C=O, Q is absent, Y is selected from NH and N—$C_{1-6}$alkyl, and $R^6$ and $R^7$ together are $C_{1-3}$alkyl-Y—$C_{1-3}$alkyl. In another preferred embodiment, L is C=O, Y is absent, and $R^6$ and $R^7$ together are $C_{1-3}$alkyl-Y—$C_{1-3}$alkyl. In another preferred embodiment, L and A are C=O, and $R^6$ and $R^7$ together are $C_{1-2}$alkyl-ZA-$C_{1-2}$alkyl. In another preferred embodiment, L and A are C=O and $R^6$ and $R^7$ together are $C_{2-3}$alkyl-A.

In certain embodiments, a compound of formula I has the following stereochemistry:

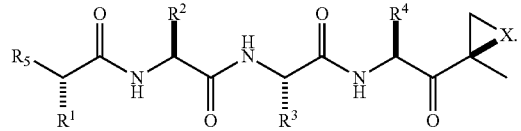

In preferred embodiments, the inhibitor has a structure of formula II or a pharmaceutically acceptable salt thereof,

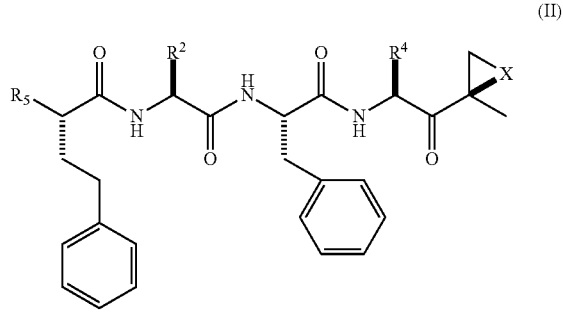

wherein each A is independently selected from C=O, C=S, and $SO_2$, preferably C=O; or A is optionally a covalent bond when adjacent to an occurrence of Z;

L is absent or is selected from C=O, C=S, and SO$_2$, preferably L is absent or C=O;

M is absent or is C$_{1-12}$alkyl, preferably C$_{1-8}$alkyl;

Q is absent or is selected from O, NH, and N—C$_{1-6}$alkyl, preferably Q is absent, O, or NH, most preferably Q is absent or O;

X is selected from O, NH, and N—C$_{1-6}$alkyl, preferably O;

Y is absent or is selected from O, NH, N—C$_{1-6}$alkyl, S, SO, SO$_2$, CHOR$^{10}$, and CHCO$_2$R$^{10}$;

each Z is independently selected from O, S, NH, and N—C$_{1-6}$alkyl, preferably O; or Z is optionally a covalent bond when adjacent to an occurrence of A;

R$^2$ and R$^4$ are each independently selected from C$_{1-6}$alkyl, C$_{1-6}$hydroxyalkyl, C$_{1-6}$alkoxyalkyl, aryl, and C$_{1-6}$aralkyl, any of which is optionally substituted with one or more of amide, amine, carboxylic acid (or a salt thereof), ester (including C$_{1-5}$ alkyl ester and aryl ester), thiol, or thioether substituents;

R$^5$ is N(R$^6$)LQR$^7$;

R$^6$ is selected from hydrogen, OH, and C$_{1-6}$alkyl, preferably C$_{1-6}$alkyl;

R$^7$ is selected from hydrogen, C$_{1-6}$alkyl, C$_{1-6}$alkenyl, C$_{1-6}$alkynyl, aryl, C$_{1-6}$aralkyl, heteroaryl, C$_{1-6}$heteroaralkyl, R$^8$ZAZ-C$_{1-8}$alkyl-, R$^{11}$Z—C$_{1-8}$alkyl-, (R$^8$O)(R$^9$O)P(=O)O—C$_{1-8}$alkyl-ZAZ-C$_{1-8}$alkyl-, R$^8$ZAZ-C$_{1-8}$alkyl-ZAZ-C$_{1-8}$alkyl-, heterocyclylMZAZ-C$_{1-8}$alkyl-, (R$^8$O)(R$^9$O)P(=O)O—C$_{1-8}$alkyl-, (R$^{10}$)$_2$N—C$_{1-12}$alkyl-, (R$^{10}$)$_3$N$^+$—C$_{1-12}$alkyl-, heterocyclylM-, carbocyclylM-, R$^{11}$SO$_2$C$_{1-8}$alkyl-, and R$^{11}$SO$_2$NH; preferably C$_{1-6}$alkyl, C$_{1-6}$alkenyl, C$_{1-6}$alkynyl, aryl, C$_{1-6}$aralkyl, heteroaryl, C$_{1-6}$heteroaralkyl, R$^8$ZA-C$_{1-8}$alkyl-, R$^{11}$Z—C$_{1-8}$alkyl-, (R$^8$O)(R$^9$O)P(=O)O—C$_{1-8}$alkyl-ZAZ-C$_{1-8}$alkyl-, (R$^8$O)(R$^9$O)P(=O)O—C$_{1-8}$alkyl-Z—C$_{1-8}$alkyl-, R$^8$ZA-C$_{1-8}$alkyl-ZAZ-C$_{1-8}$alkyl-, heterocyclylMZAZ-C$_{1-8}$alkyl-, (R$^8$O)(R$^9$O)P(=O)O—C$_{1-8}$alkyl-, (R$^{10}$)$_2$N—C$_{1-8}$alkyl-, (R$^{10}$)$_3$N$^+$—C$_{1-8}$alkyl-, heterocyclylM-, carbocyclylM-, R$^{11}$SO$_2$C$_{1-8}$alkyl-, and R$^{11}$SO$_2$NH, wherein each occurrence of Z and A is independently other than a covalent bond; or R$^6$ and R$^7$ together are C$_{1-6}$alkyl-Y—C$_{1-6}$alkyl, C$_{1-6}$alkyl-ZAZ-C$_{1-6}$alkyl, ZAZ-C$_{1-6}$alkyl-ZAZ-C$_{1-6}$alkyl, ZAZ-C$_{1-6}$ alkyl-ZAZ, or C$_{1-6}$alkyl-A, thereby forming a ring; preferably C$_{1-2}$alkyl-Y—C$_{1-2}$alkyl, C$_{1-2}$alkyl-ZA-C$_{1-2}$alkyl, A-C$_{1-2}$alkyl-ZA-C$_{1-2}$alkyl, A-C$_{1-3}$alkyl-A, or C$_{1-4}$alkyl-A, wherein each occurrence of Z and A is independently other than a covalent bond;

R$^8$ and R$^9$ are independently selected from hydrogen, metal cation, C$_{1-6}$alkyl, C$_{1-6}$alkenyl, C$_{1-6}$alkynyl, aryl, heteroaryl, C$_{1-6}$aralkyl, and C$_{1-6}$heteroaralkyl, preferably from hydrogen, metal cation, and C$_{1-6}$alkyl, or R$^8$ and R$^9$ together are C$_{1-6}$alkyl, thereby forming a ring;

each R$^{10}$ is independently selected from hydrogen and C$_{1-6}$alkyl, preferably C$_{1-6}$alkyl; and R$^{11}$ is independently selected from hydrogen, C$_{1-6}$alkyl, C$_{1-6}$alkenyl, C$_{1-6}$alkynyl, carbocyclyl, heterocyclyl, aryl, heteroaryl, C$_{1-6}$aralkyl, and C$_{1-6}$heteroaralkyl, provided that when R$^6$ is H or CH$_3$ and Q is absent, LR$^7$ is not hydrogen, unsubstituted C$_{1-6}$alkylC=O, a further chain of amino acids, t-butoxycarbonyl (Boc), benzoyl (Bz), fluoren-9-ylmethoxycarbonyl (Fmoc), triphenylmethyl(trityl), benzyloxycarbonyl (Cbz), trichloroethoxycarbonyl (Troc); or substituted or unsubstituted aryl or heteroaryl; and in any occurrence of the sequence ZAZ, at least one member of the sequence must be other than a covalent bond.

In certain embodiments, L is C=O, Q is absent, X is O, R$^6$ is H, and R$^2$ and R$^4$ are selected from C$_{1-6}$alkyl and C$_{1-6}$aralkyl. In preferred such embodiments, R$^2$ and R$^4$ are C$_{1-6}$alkyl. In the most preferred such embodiment, R$^2$ and R$^4$ are isobutyl.

In certain embodiments, L is C=O, Q is absent, X is O, R$^6$ is H, R$^2$ and R$^4$ are isobutyl, and R$^7$ is heterocyclylM-, where the heterocycle is a nitrogen-containing heterocycle, such as piperazino (including N-(lower alkyl)piperazino), morpholino, and piperidino. In preferred such embodiments, M is CH$_2$.

In certain embodiments, a compound of formula II is selected from:

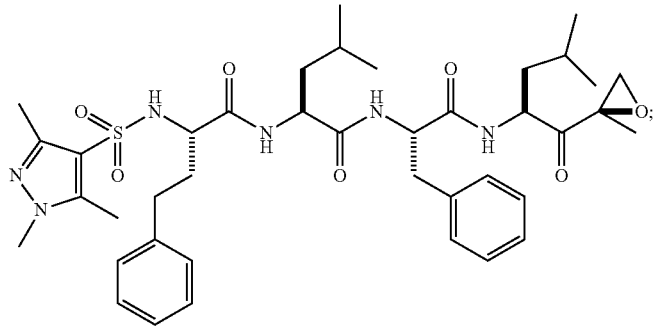

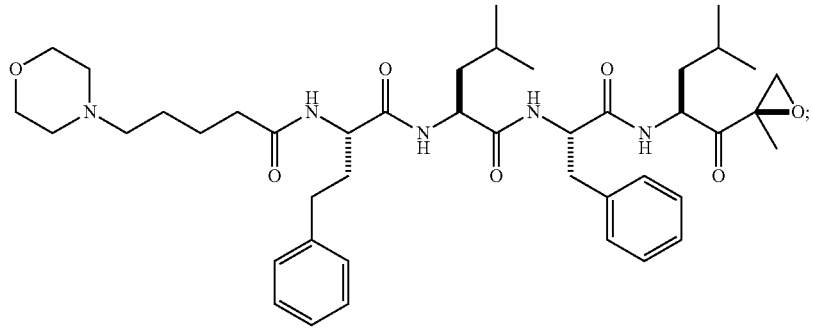

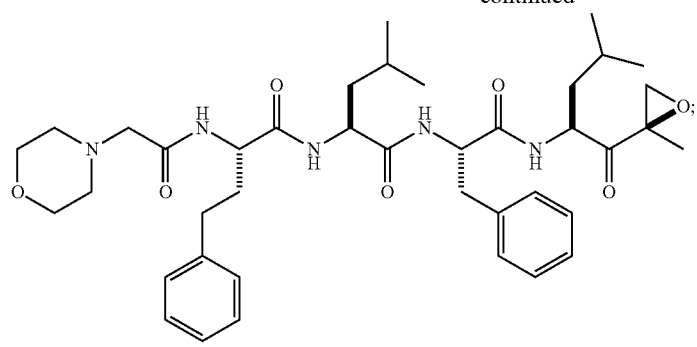
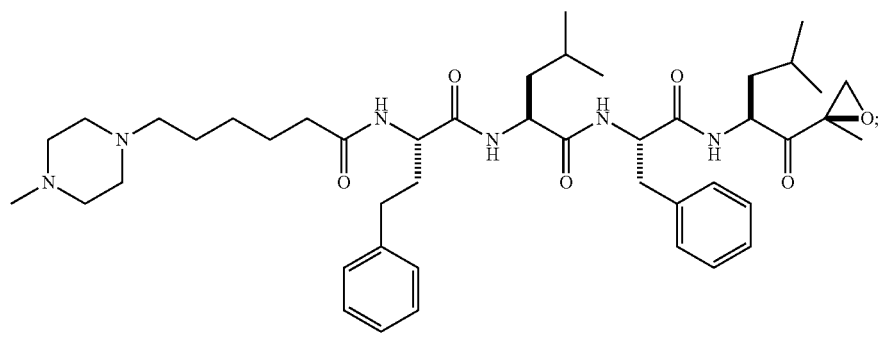
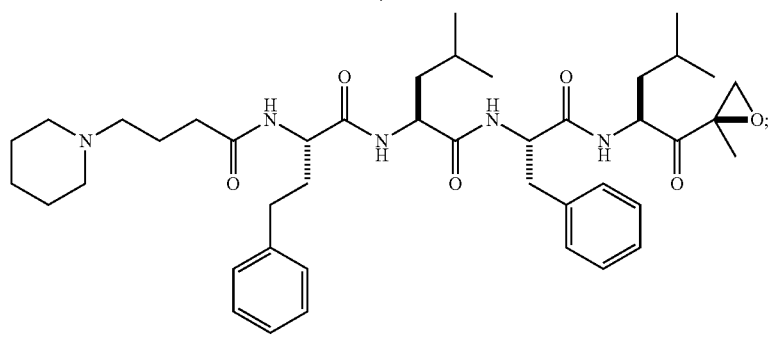
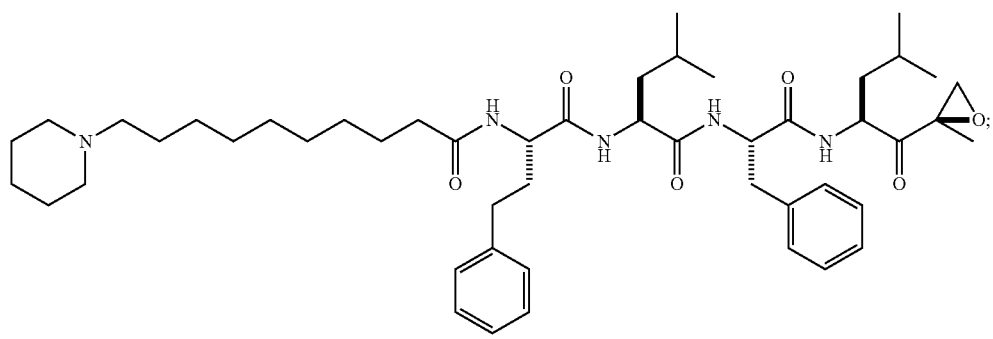
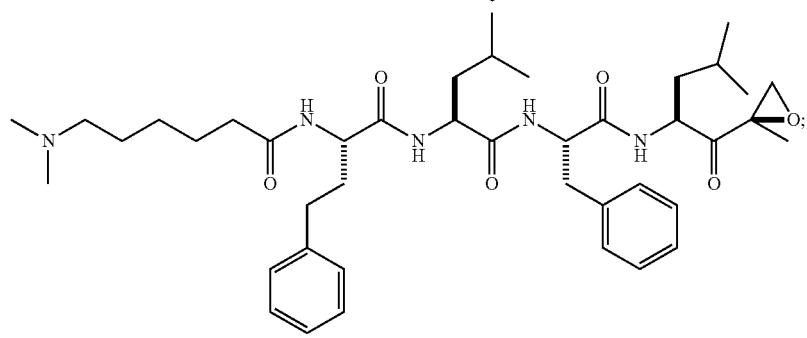

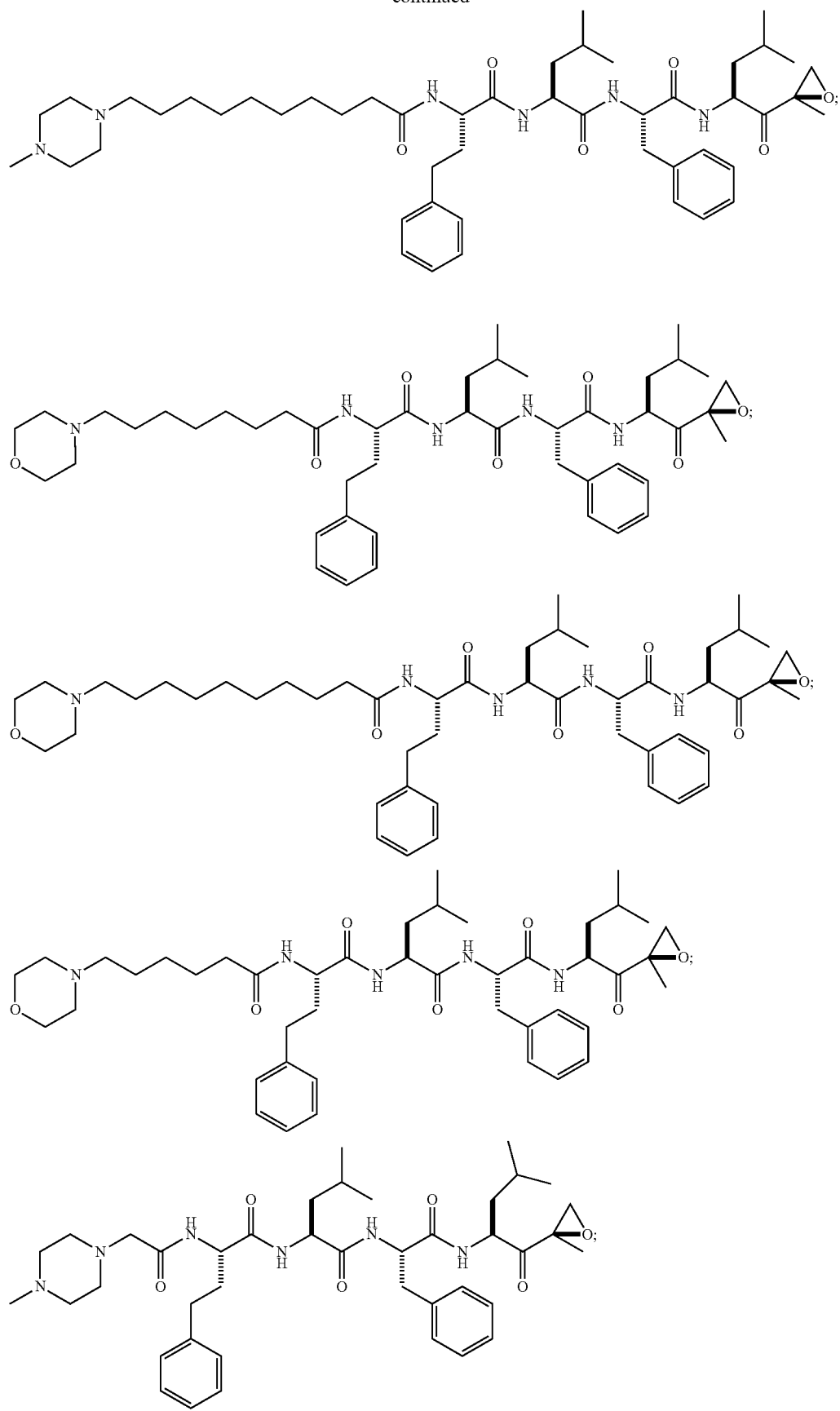

-continued
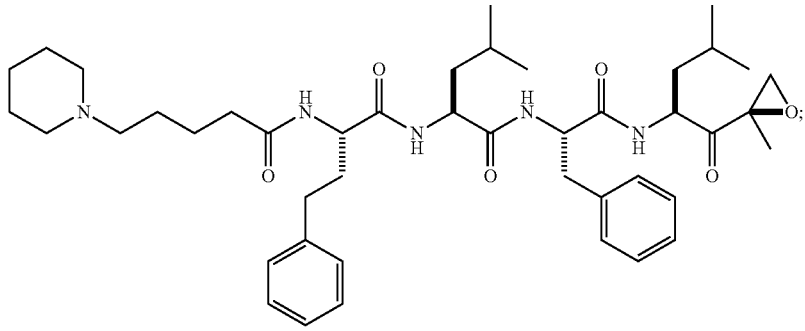
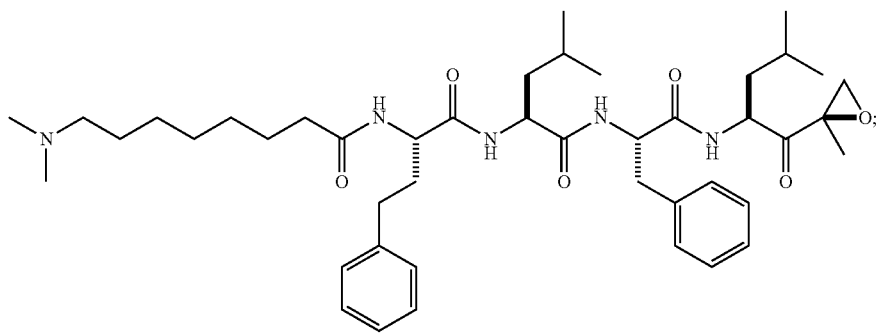
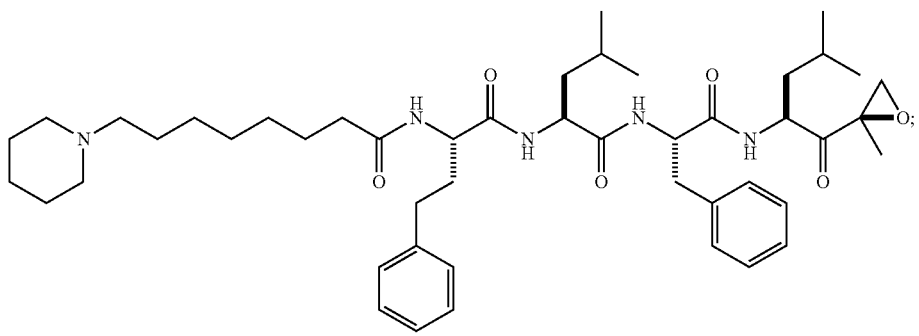
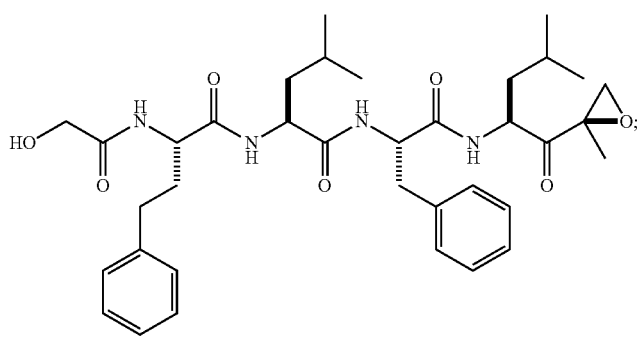
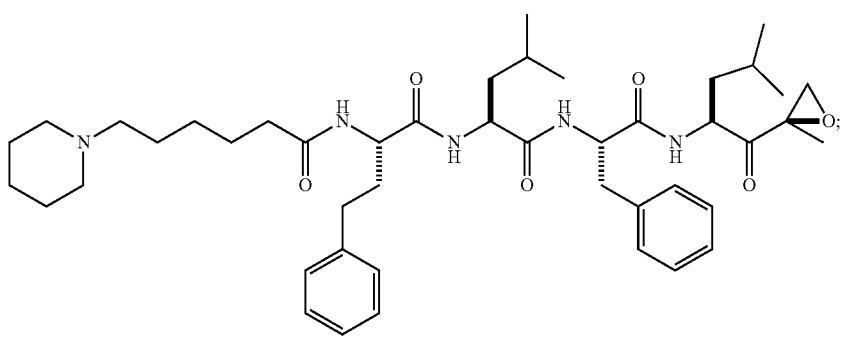

-continued
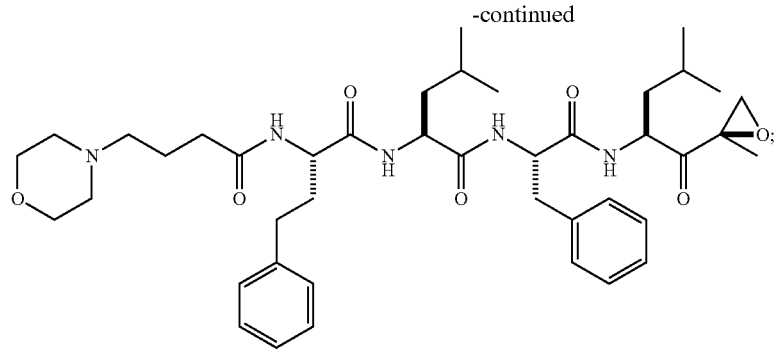
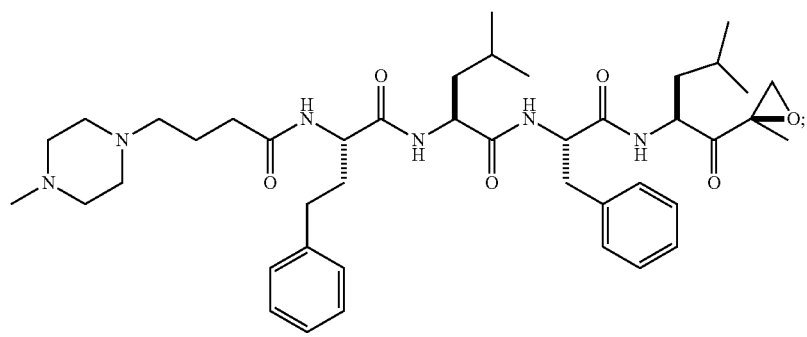
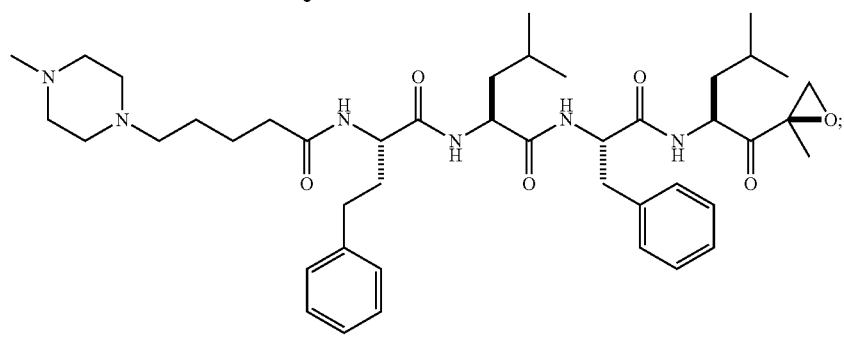
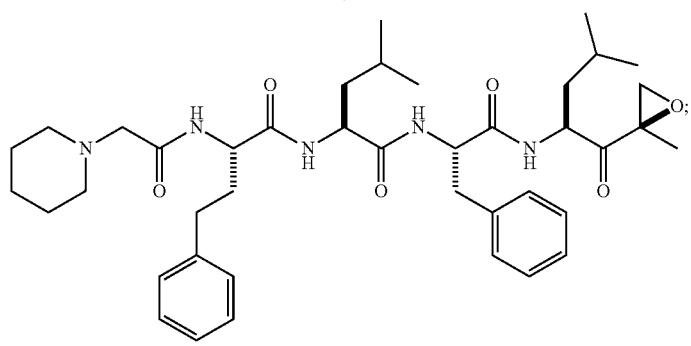
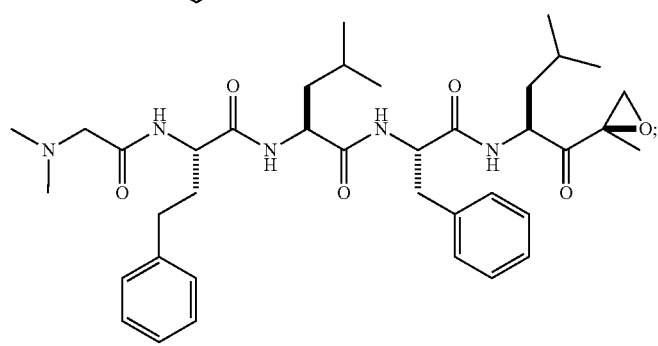

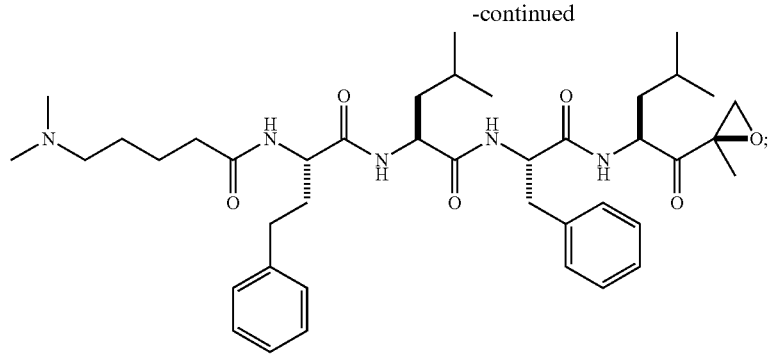
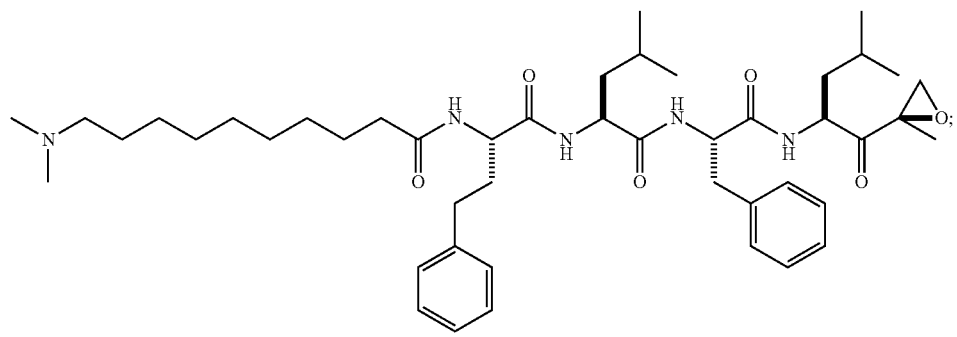
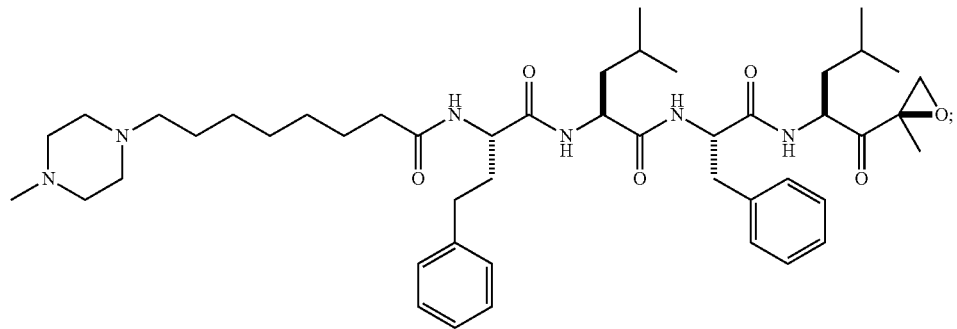
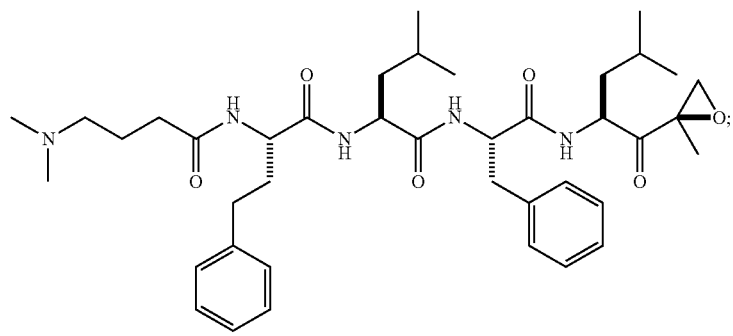
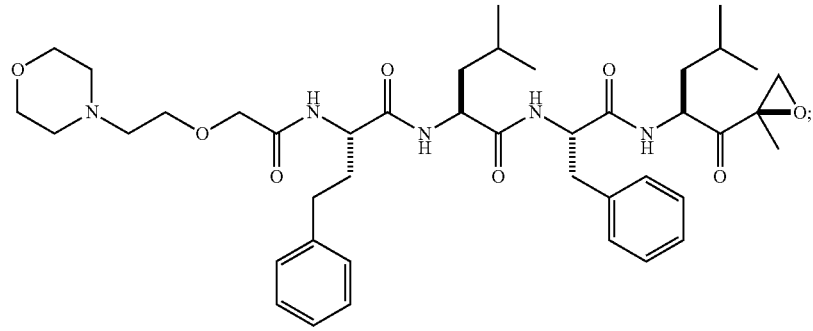

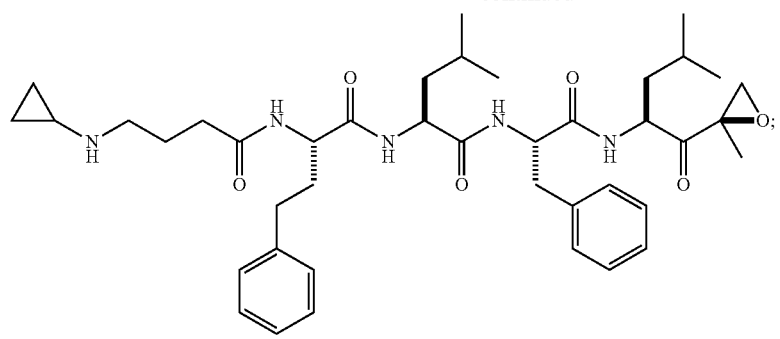
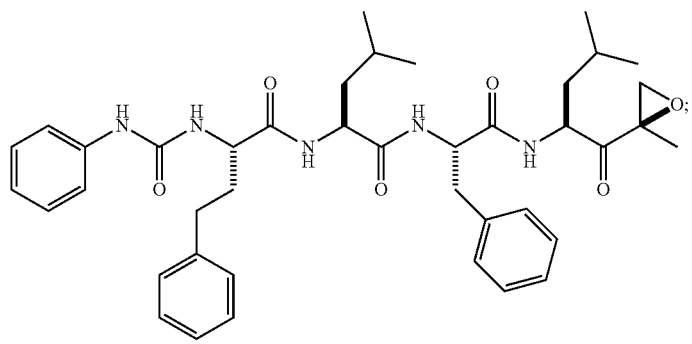
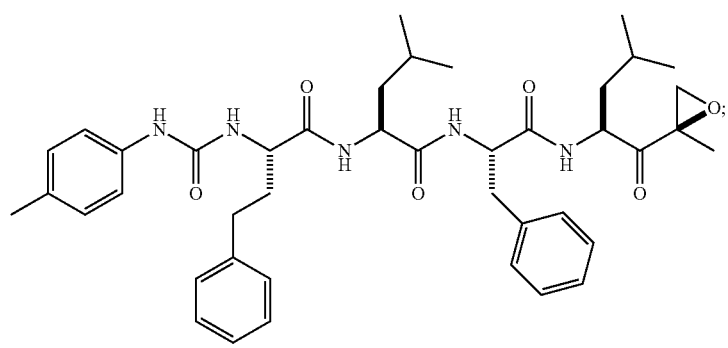
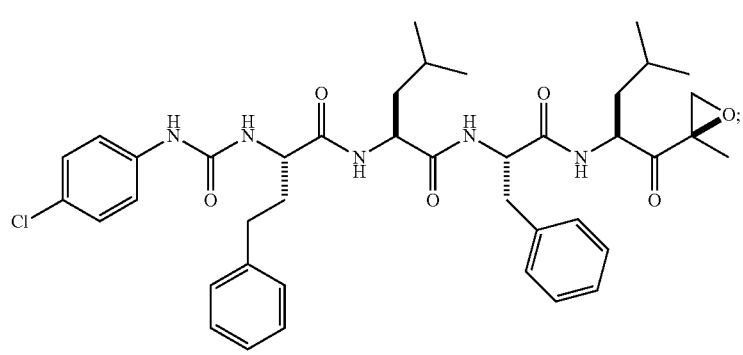
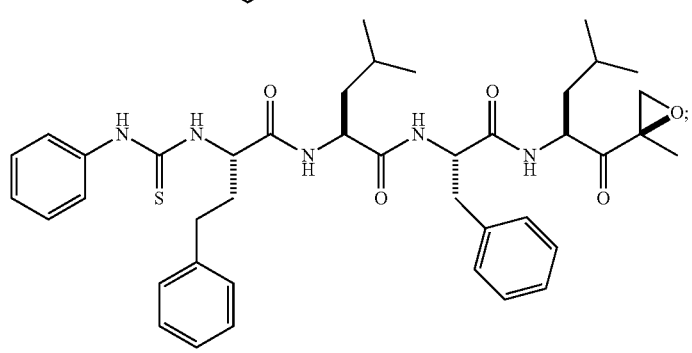

-continued

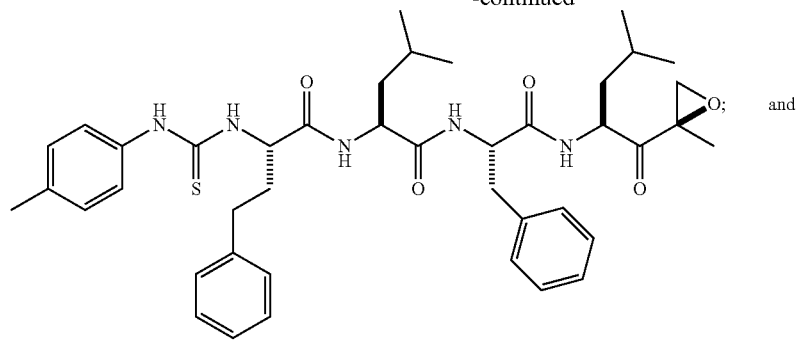 and

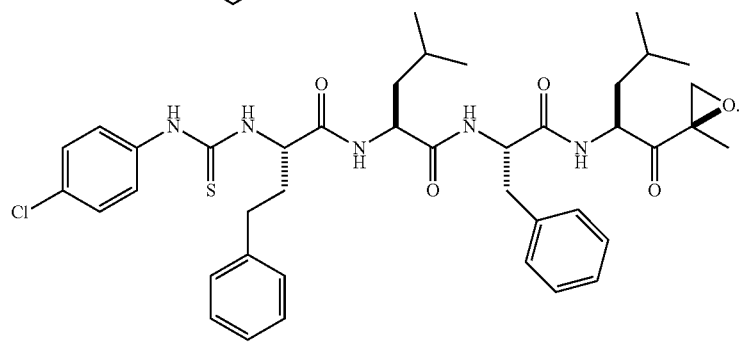

In certain embodiments, the subject compounds are phosphate-containing prodrugs of the compounds disclosed in U.S. application Ser. No. 09/569,748, the contents of which are hereby incorporated by reference in their entirety. The enzyme inhibitor prodrugs for inhibition of chymotrypsin-like (CT-L) activity of Ntn have a structure of formula (III) or a pharmaceutically acceptable salt thereof (III)

wherein

X is selected from O, NH, and N-alkyl, preferably O;

$R^1$, $R^2$, $R^3$, and $R^4$ are independently selected from hydrogen and a group of formula IV, with the proviso that at least one of $R^1$, $R^2$, $R^3$, and $R^4$ is a group of formula IV;

IV $R^5$, $R^6$, $R^7$, and $R^8$ are independently selected from $C_{1-6}$alkyl, $C_{1-6}$hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether;

$R^9$ is a further chain of amino acids, hydrogen, $C_{1-6}$acyl, a protecting group, aryl, or heteroaryl, where substituents may include halogen, carbonyl, nitro, hydroxy, aryl, and $C_{1-5}$alkyl;

$R^{10}$ and $R^{11}$ are independently selected from hydrogen and $C_{1-6}$alkyl, or $R^{10}$ and $R^{11}$ together form a 3- to 6-membered carbocyclic or heterocyclic ring;

$R^{12}$ and $R^{13}$ are independently selected from hydrogen, a metal cation, $C_{1-6}$alkyl, and $C_{1-6}$aralkyl, or $R^{12}$ and $R^{13}$ together represent $C_{1-6}$alkyl, thereby forming a ring; and L is absent or is selected from $—CO_2$ or $—C(=S)O$.

Suitable N-terminal protecting groups known in the art of peptide syntheses, include t-butoxy carbonyl (Boc), benzoyl (Bz), fluoren-9-ylmethoxycarbonyl (Fmoc), triphenylmethyl (trityl) and trichloroethoxycarbonyl (Troc) and the like. The use of various N-protecting groups, e.g., the benzyloxy carbonyl group or the t-butyloxycarbonyl group (Boc), various coupling reagents, e.g., dicyclohexylcarbodiimide (DCC), 1,3-diisopropylcarbodiimide (DIC), 1-(3-dimethylaminopropyl)-3-ethylcarbodiimide (EDC), N-hydroxyazabenzotriazole (HATU), carbonyldiimidazole, or 1-hydroxybenzotriazole monohydrate (HOBT), and various cleavage conditions: for example, trifluoracetic acid (TFA), HCl in dioxane, hydrogenation on Pd—C in organic solvents (such as methanol or ethyl acetate), boron tris(trifluoroacetate), and cyanogen bromide, and reaction in solution with isolation and purification of intermediates are well-known in the art of peptide synthesis, and are equally applicable to the preparation of the subject compounds.

In some embodiments, any two of $R^1$, $R^2$, $R^3$, and $R^4$ are hydrogen and any two of $R^1$, $R^2$, $R^3$, and $R^4$ have a structure of formula IV. In preferred embodiments any three of $R^1$, $R^2$, $R^3$, and $R^4$ are hydrogen and any one of $R^1$, $R^2$, $R^3$, and $R^4$ has a structure of formula IV. In the most preferred embodiment, $R^1$ has a structure of formula IV and $R^2$, $R^3$, and $R^4$ are hydrogen.

In certain embodiments, $R^5$, $R^6$, $R^7$, and $R^8$ are $C_{1-6}$alkyl or $C_{1-6}$aralkyl. In preferred embodiments, $R^6$ and $R^8$ are $C_{1-6}$alkyl and $R^5$ and $R^7$ are $C_{1-6}$aralkyl. In the most preferred embodiment, $R^6$ and $R^8$ are isobutyl, $R^5$ is 2-phenylethyl, and $R^7$ is phenylmethyl. In certain embodiments, $R^9$ is selected from hydrogen, $C_{1-6}$acyl, or a protecting group. In preferred embodiments, $R^9$ is hydrogen or acetyl. In the most preferred embodiment, $R^9$ is acetyl.

In certain embodiments, $R^{10}$ and $R^{11}$ are selected from hydrogen and $C_{1-6}$alkyl. In a preferred embodiment, $R^{10}$ is hydrogen and $R^{11}$ is $C_{1-6}$alkyl. In a further preferred embodiment, $R^{10}$ is hydrogen and $R^{11}$ is methyl. In another preferred embodiment, both $R^{10}$ and $R^{11}$ are hydrogen. In certain embodiments, $R^{12}$ and $R^{13}$ are $C_{1-6}$alkyl, metal cation, or $C_{1-6}$aralkyl. In certain preferred embodiments, $R^{12}$ and $R^{13}$ are selected from benzyl, tert-butyl, and sodium cation. In more preferred embodiments, both $R^{12}$ and $R^{13}$ are benzyl or tert-butyl. In the most preferred embodiment, at least one of $R^{12}$ and $R^{13}$ is a sodium cation.

In certain embodiments, a compound of formula III has the following stereochemistry:

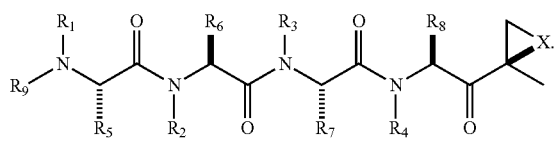

In preferred embodiments, the inhibitor has a structure of formula V or a pharmaceutically acceptable salt thereof,

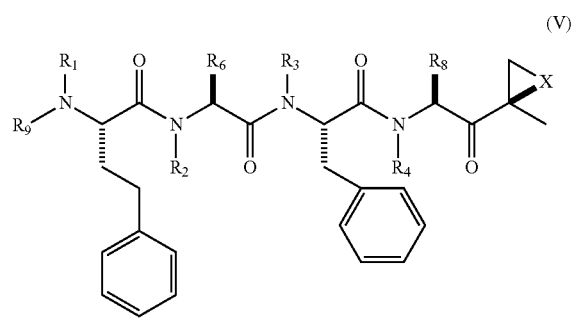

(V)

wherein

X is selected from O, NH, and N-alkyl, preferably O;

$R^1$, $R^2$, $R^3$, and $R^4$ are independently selected from hydrogen and a group of formula IV, with the proviso that at least one of $R^1$, $R^2$, $R^3$, and $R^4$ is a group of formula IV;

$R^6$ and $R^8$ are independently selected from $C_{1-6}$alkyl, $C_{1-6}$hydroxy alkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether;

$R^9$ is a further chain of amino acids, hydrogen, acyl, a protecting group, aryl, or heteroaryl, where substituents may include halogen, carbonyl, nitro, hydroxy, aryl, and $C_{1-5}$alkyl. Suitable N-terminal protecting groups known in the art of peptide syntheses, include t-butoxy carbonyl (Boc), benzoyl (Bz), fluoren-9-ylmethoxycarbonyl (Fmoc), triphenylmethyl (trityl) and trichloroethoxycarbonyl (Troc) and the like; and In some embodiments, any two of $R^1$, $R^2$, $R^3$, and $R^4$ are hydrogen and any two of $R^1$, $R^2$, $R^3$, and $R^4$ have a structure of formula IV. In preferred embodiments any three of $R^1$, $R^2$, $R^3$, and $R^4$ are hydrogen and any one of $R^1$, $R^2$, $R^3$, and $R^4$ has a structure of formula IV. In the most preferred embodiment, $R^1$ has a structure of formula IV and $R^2$, $R^3$, and $R^4$ are hydrogen.

In certain embodiments, $R^6$ and $R^8$ are $C_{1-6}$alkyl or $C_{1-6}$aralkyl. In preferred embodiments, $R^6$ and $R^8$ are $C_{1-6}$alkyl. In the most preferred embodiment, $R^6$ and $R^8$ are isobutyl. In certain embodiments, $R^9$ is selected from hydrogen, $C_{1-6}$acyl, or a protecting group. In preferred embodiments, $R^9$ is hydrogen or acetyl. In the most preferred embodiment, $R^9$ is acetyl.

In certain embodiments, $R^{10}$ and $R^{11}$ are selected from hydrogen and $C_{1-6}$alkyl. In a preferred embodiment, $R^{10}$ is hydrogen and $R^{11}$ is $C_{1-6}$alkyl. In a further preferred embodiment, $R^{10}$ is hydrogen and $R^{11}$ is methyl. In another preferred embodiment, both $R^{10}$ and $R^{11}$ are hydrogen. In certain embodiments, $R^{12}$ and $R^{13}$ are $C_{1-6}$alkyl, metal cation, or $C_{1-6}$aralkyl. In certain preferred embodiments, $R^{12}$ and $R^{13}$ are selected from benzyl, tert-butyl, and sodium cation. In more preferred embodiments, both $R^{12}$ and $R^{13}$ are benzyl or tert-butyl. In the most preferred embodiment, at least one of $R^{12}$ and $R^{13}$ is a sodium cation.

In certain embodiments, $R^6$ and $R^8$ are $C_{1-6}$alkyl. In preferred embodiments, $R^6$ and $R^8$ are isobutyl. In preferred embodiments, $R^9$ is hydrogen or acetyl. In the most preferred embodiments, $R^9$ is acetyl. In a preferred embodiment, $R^{10}$ is hydrogen and $R^{11}$ is methyl. In another preferred embodiment, both $R^{10}$ and $R^{11}$ are hydrogen. In certain embodiments, $R^{12}$ and $R^{13}$ are $C_{1-6}$alkyl, metal cation, or $C_{1-6}$aralkyl. In certain embodiments, $R^{12}$ and $R^{13}$ are selected from benzyl, tert-butyl, and sodium cation. In more preferred embodiments, both $R^{12}$ and $R^{13}$ are benzyl or tert-butyl. In the most preferred embodiment, at least one of $R^{12}$ and $R^{13}$ is a sodium cation.

In certain embodiments, specifically excluded compounds are disclosed in U.S. Pat. No. 6,831,099, the disclosure of which is incorporated herein by reference in its entirety.

One aspect of the invention relates to a medical device including composition disclosed herein that include an inhibitor having a structure of any one of formulae I, II, III, or V. In one embodiment, the composition is incorporated within a medical device. In certain embodiments, the medical device is a gel comprising a polymer matrix or ceramic matrix and an inhibitor. Said polymer can be either naturally occurring or synthetic. In another embodiment, said gel serves as a drug depot, an adhesive, a suture, a barrier or a sealant.

Another aspect of the invention relates to a medical device comprising a substrate having a surface onto which an inhibitor having a structure of any one of formulae I, II, III, or V is disposed. In one embodiment, the inhibitor is directly disposed on a medical device. In another embodiment, a coating is so disposed, the coating comprising a polymer matrix or ceramic matrix with an inhibitor having a structure of any one of formulae I, II, III, or V dispersed or dissolved therein.

In one embodiment, the medical device is a coronary, vascular, peripheral, or biliary stent. More particularly, the stent of the present invention is an expandable stent. When coated with a matrix containing an inhibitor having a structure any one of formulae I, II, III, or V, the matrix is flexible to accommodate compressed and expanded states of such an expandable stent. In another embodiment of this invention, the stent has at least a portion which is insertable or implantable into the body of a patient, wherein the portion has a surface which is adapted for exposure to body tissue and wherein at least a part of the surface is coated with an inhibitor having a structure of any one of formulae I, II, III, or V, or a coating comprising a matrix having an inhibitor having a structure of any one of formulae I, II, III, or V is dispersed or dissolved therein. An example of a suitable stent is disclosed in U.S. Pat. No. 4,733,665, which is incorporated herein by reference in its entirety.

In another embodiment, the medical device of the present invention is a surgical implement such as a vascular implant, an intraluminal device, surgical sealant or a vascular support. More particularly, the medical device of the present invention is a catheter, an implantable vascular access port, a central venous catheter, an arterial catheter, a vascular graft, an intraaortic balloon pump, a suture, a ventricular assist pump, a drug-eluting barrier, an adhesive, a vascular wrap, an extra/perivascular support, a blood filter, or a filter adapted for deployment in a blood vessel, coated with an inhibitor having a structure of any one of formulae I, II, III, or V either directly or by a matrix containing an inhibitor having a structure of any one of formulae I, II, III, or V.

In certain embodiments, the intraluminal medical device is coated with an inhibitor having a structure of any one of formulae I, II, III, or V or a coating comprising biologically tolerated matrix and an inhibitor having a structure of any one of formulae I, II, III, or V dispersed in the polymer, said device having an interior surface and an exterior surface, having the coating applied to at least a part of the interior surface, the exterior surface, or both.

In certain embodiments, the medical device may be useful to prevent restenosis after angioplasty. The medical device may also be useful for the treatment of various diseases and conditions by providing localized administration of an inhibitor having a structure of any one of formulae I, II, III, or V. Such diseases and conditions include restenosis, inflammation, rheumatoid arthritis, tissue injury due to inflammation, hyperproliferative diseases, severe or arthritic psoriasis, muscle-wasting diseases, chronic infectious diseases, abnormal immune response, conditions involving vulnerable plaques, injuries related to ischemic conditions, and viral infection and proliferation. Examples of diseases and conditions that are subject to a treatment including the drug coated medical devices of the present invention include atherosclerosis, acute coronary syndrome, Alzheimer's disease, cancer, fever, muscle disuse (atrophy), denervation, vascular occlusions, stroke, HIV infection, nerve injury, renal failure associated with acidosis, and hepatic failure. See, e.g., Goldberg, U.S. Pat. No. 5,340,736.

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$alkoxyalkyl" refers to a $C_{1-6}$alkyl group substituted with an alkoxy group, thereby forming an ether.

The term "$C_{1-6}$aralkyl", as used herein, refers to a $C_{1-6}$alkyl group substituted with an aryl group.

The terms "amine" and "amino" are art-recognized and refer to both unsubstituted and substituted amines and salts thereof, e.g., a moiety that can be represented by the general formulae:

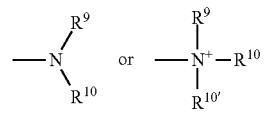

wherein $R^9$, $R^{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or —$(CH_2)_m$—$R^8$. In certain embodiments, an amino group is basic, meaning it has a $pK_a \geq 7.00$. The protonated forms of these functional groups have $pK_a$s above 7.00.

The terms "amide" and "amido" are art-recognized as an amino-substituted carbonyl and includes a moiety that can be represented by the general formula:

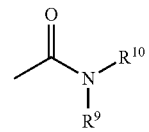

wherein $R^9$, $R^{10}$ are as defined above. Preferred embodiments of the amide will not include imides which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "carbonyl" is art-recognized and includes such moieties as can be represented by the general formula:

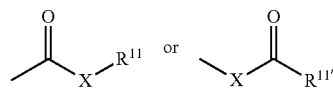

wherein X is a bond or represents an oxygen or a sulfur, and $R^{11}$ represents a hydrogen, an alkyl, an alkenyl, $-(CH_2)_m-R^8$ or a pharmaceutically acceptable salt, $R^{11'}$ represents a hydrogen, an alkyl, an alkenyl or $-(CH_2)_m-R^8$, where m and $R^8$ are as defined above. Where X is an oxygen and $R^{11}$ or $R^{11'}$ is not hydrogen, the formula represents an "ester". Where X is an oxygen, and $R^{11}$ is a hydrogen, the formula represents a "carboxylic acid".

As used herein, "enzyme" can be any partially or wholly proteinaceous molecule which carries out a chemical reaction in a catalytic manner. Such enzymes can be native enzymes, fusion enzymes, proenzymes, apoenzymes, denatured enzymes, farnesylated enzymes, ubiquitinated enzymes, fatty acylated enzymes, gerangeranylated enzymes, GPI-linked enzymes, lipid-linked enzymes, prenylated enzymes, naturally-occurring or artificially-generated mutant enzymes, enzymes with side chain or backbone modifications, enzymes having leader sequences, and enzymes complexed with non-proteinaceous material, such as proteoglycans, proteoliposomes. Enzymes can be made by any means, including natural expression, promoted expression, cloning, various solution-based and solid-based peptide syntheses, and similar methods known to those of skill in the art.

The term "$C_{1-6}$heteroaralkyl", as used herein, refers to a $C_{1-6}$alkyl group substituted with a heteroaryl group.

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "$C_{1-6}$hydroxyalkyl" refers to a $C_{1-6}$alkyl group substituted with a hydroxy group.

As used herein, the term "inhibitor" is meant to describe a compound that blocks or reduces an activity of an enzyme (for example, inhibition of proteolytic cleavage of standard fluorogenic peptide substrates such as suc-LLVY-AMC (SEQ ID NO: 1), Box-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme.

As used herein, the term "peptide" includes not only standard amide linkage with standard α-substituents, but commonly utilized peptidomimetics, other modified linkages, non-naturally occurring side chains, and side chain modifications, as detailed below.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "proteasome" as used herein is meant to include immuno- and constitutive proteasomes.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "thioether" refers to an alkyl group, as defined above, having a sulfur moiety attached thereto. In preferred embodiments, the "thioether" is represented by —S-alkyl. Representative thioether groups include methylthio, ethylthio, and the like.

As used herein, the term "treating" or "treatment" includes reversing, reducing, or arresting the symptoms, clinical signs, and underlying pathology of a condition in manner to improve or stabilize a subject's condition.

Selectivity for 20S Proteasome

The enzyme inhibitor analogs and prodrugs disclosed herein are useful in part because they inhibit the action of the 20S proteasome. Additionally, unlike other 20S proteasome inhibitors, the compounds disclosed herein are highly selective toward the 20S proteasome, with respect to other protease enzymes. That is, the instant compounds show selectivities for the 20S proteasome over other proteases such as cathepsins, calpains, papain, chymotrypsin, trypsin, tripeptidyl pepsidase II. The selectivities of the enzyme inhibitors for 20S proteasome are such that at concentrations below about 50 μM, the enzyme inhibitors show inhibition of the catalytic activity of the 20S proteasome, while not showing inhibition of the catalytic activity of other proteases such as cathepsins, calpains, papain, chymotrypsin, trypsin, tripeptidyl pepsidase II. In preferred embodiments, the enzyme inhibitors show inhibition of the catalytic activity of the 20S proteasome at concentrations below about 10 μM, while not showing inhibition of the catalytic activity of other proteases at these concentrations. In even more preferred embodiments, the enzyme inhibitors show inhibition of the catalytic activity of the 20S proteasome at concentrations below about 1 μM, while not showing inhibition of the catalytic activity of other proteases at these concentrations. Enzyme kinetic assays are disclosed in U.S. application Ser. No. 09/569,748, Example 2 and Stein et al., *Biochem.* (1996), 35, 3899-3908.

Selectivity for Chymotrypsin-Like Activity

Particular embodiments of the enzyme inhibiting analog and prodrug compounds described herein are further useful because they can efficiently and selectively inhibit the chymotrypsin-like activity of the 20S proteasome, as compared to the trypsin-like, and PGPH activities. The chymotrypsin-like activity of 20S proteasome is characterized by cleavage of peptides in the immediate vicinity of large hydrophobic residues. In particular, the chymotrypsin-like activity of Ntn hydrolases can be determined by cleavage of a standard substrate. Examples of such substrates are known in the art. For example, a leucylleucylvalinyltyrosine derivative can be used. Enzyme kinetic assays are disclosed in U.S. application Ser. No. 09/569,748, Example 2 and Stein et al., *Biochem.* (1996), 35, 3899-3908.

Uses of Enzyme Inhibitors

The biological consequences of proteasome inhibition are numerous. At the cellular level, the accumulation of polyubiquitinated proteins, cell morphological changes, and apoptosis have been reported upon treatment of cells with various proteasome inhibitors. Proteasome inhibition has also been suggested as a possible antitumor therapeutic strategy. The fact that epoxomicin was initially identified in a screen for antitumor compounds validates the proteasome as an antitumor chemotherapeutic target. Accordingly, these compounds are useful for treating cancer. Proteasome inhibition has also been associated with inhibition of NF-κB activation and stabilization of p53 levels. Thus, compounds of the invention may also be used to inhibit NF-κB activation, and stabilize p53 levels in cell culture. Since NF-κB is a key regulator of inflammation, it is an attractive target for anti-inflammatory therapeutic intervention. Thus, compounds of the invention may be useful for the treatment of conditions associated with chronic inflammation, including, but not limited to COPD, psoriasis, bronchitis, emphysema, and cystic fibrosis.

The disclosed compounds can be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins and transcription factor NF-κB.

Another embodiment of the invention is the use of the compounds disclosed herein for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDs dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser (SEQ ID NO: 2), which is identical to the β-subunit of human macropain (Kojima, S. et al., *Fed. Eur. Biochem. Soc.*, (1992) 304:57-60). The APP-processing enzyme cleaves at the $Gln^{15}$-$Lys^{16}$ bond; in the presence of calcium ion, the enzyme also cleaves at the Met-$^1$-$Asp^1$ bond, and the $Asp^1$-$Ala^2$ bonds to release the extracellular domain of β-AP.

One embodiment, therefore, is a method of treating Alzheimer's disease, including administering to a subject an effective amount of a compound (e.g., pharmaceutical composition) disclosed herein. Such treatment includes reducing the rate of β-AP processing, reducing the rate of β-AP plaque formation, reducing the rate of β-AP generation, and reducing the clinical signs of Alzheimer's disease.

Other embodiments of the invention relate to cachexia and muscle-wasting diseases. The proteasome degrades many proteins in maturing reticulocytes and growing fibroblasts. In cells deprived of insulin or serum, the rate of proteolysis nearly doubles Inhibiting the proteasome reduces proteolysis, thereby reducing both muscle protein loss and the nitrogenous load on kidneys or liver. Inhibitors of the invention are useful for treating conditions such as cancer, chronic infectious diseases, fever, muscle disuse (atrophy) and denervation, nerve injury, fasting, renal failure associated with acidosis, diabetes, and hepatic failure. See, e.g., Goldberg, U.S. Pat. No. 5,340,736. Embodiments of the invention therefore encompass methods for: reducing the rate of muscle protein degradation in a cell; reducing the rate of intracellular protein degradation; reducing the rate of degradation of p53 protein in a cell; and inhibiting the growth of p53-related cancers. Each of these methods includes contacting a cell (in vivo or in vitro, e.g., a muscle in a subject) with an effective amount of a compound (e.g., pharmaceutical composition) disclosed herein.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes (Palombella et al., *Cell* (1994) 78:773-785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., *Cell* (1994) 78:773-785). Some embodiments of the invention include methods of affecting the level of expression of IL-2, MHC-I, IL-6, TNFα, IFN-β or any of the other previously-mentioned proteins, each method including administering to a subject an effective amount of a compound disclosed herein. Complexes including p50 are rapid mediators of acute inflammatory and immune responses (Thanos, D. and Maniatis, T., *Cell* (1995) 80:529-532).

NF-κB also participates in the expression of the cell adhesion genes that encode E-selectin, P-selectin, ICAM, and VCAM-1 (Collins, T., *Lab. Invest*. (1993) 68:499-508). One embodiment of the invention is a method for inhibiting cell adhesion (e.g., cell adhesion mediated by E-selectin, P-selectin, ICAM, or VCAM-1), including contacting a cell with (or administering to a subject) an effective amount of a compound (or a pharmaceutical composition) disclosed herein.

NF-κB also binds specifically to the HIV-enhancer/promoter. When compared to the Nef of mac239, the HIV regulatory protein Nef of pbj14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., *Science*, (1995) 267:960). Two embodiments of the invention are a method for inhibiting or reducing HIV infection in a subject, and a method for decreasing the level of viral gene expression, each method including administering to the subject an effective amount of a compound disclosed herein.

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., *J. Immun.* (2003) 171: 1515-1525). Therefore, in certain embodiments, compounds of the invention may be used for the inhibition of TNFα to prevent and/or treat septic shock.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to a compound described herein. A compound of the invention may be used to treat immune-related conditions such as allergy, asthma, organ/tissue rejection (graft-versus-host disease), and auto-immune diseases, including, but not limited to, lupus, rheumatoid arthritis, psoriasis, multiple sclerosis, and inflammatory bowel diseases (such as ulcerative colitis and Crohn's disease). Thus, a further embodiment is a method for suppressing the immune system of a subject (e.g., inhibiting transplant rejection, allergies, and asthma), including administering to the subject an effective amount of a compound described herein.

Another further embodiment is a method for altering the repertoire of antigenic peptides produced by the proteasome or other Ntn with multicatalytic activity. For example, if the PGPH activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of chymotrypsin-like activity of the proteasome.

Certain proteasome inhibitors block both degradation and processing of ubiquitinated NF-κB in vitro and in vivo. Proteasome inhibitors also block IκB-α degradation and NF-κB activation (Palombella, et al. *Cell* (1994) 78:773-785; and Traenckner, et al., *EMBO J.* (1994) 13:5433-5441). One embodiment of the invention is a method for inhibiting IκB-α degradation, including contacting the cell with a compound described herein. A further embodiment is a method for reducing the cellular content of NF-κB in a cell, muscle, organ, or subject, including contacting the cell, muscle, organ, or subject with a compound described herein.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Other embodiments of the invention are methods for affecting cyclin-dependent eukaryotic cell cycles, including exposing a cell (in vitro or in vivo) to a compound disclosed herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed all cyclins are associated with p34.sup.cdc2 protein kinase or related kinases. The proteolysis targeting signal is localized to amino acids 42-RAALGNISEN-50 (SEQ ID NO: 3) (destruction box). There is evidence that cyclin is converted to a form vulnerable to a ubiquitin ligase or that a cyclin-specific ligase is activated during mitosis (Ciechanover, A., Cell, (1994) 79:13-21). Inhibition of the proteasome inhibits cyclin degradation, and therefore inhibits cell proliferation, for example, in cyclin-related cancers (Kumatori et al., Proc. Natl. Acad. Sci. USA (1990) 87:7071-7075). One embodiment of the invention is a method for treating a proliferative disease in a subject (e.g., cancer, psoriasis, or restenosis), including administering to the subject an effective amount of a compound disclosed herein. The invention also encompasses a method for treating cyclin-related inflammation in a subject, including administering to a subject a therapeutically effective amount of a compound described herein.

Additional embodiments are methods for affecting the proteasome-dependent regulation of oncoproteins and methods of treating or inhibiting cancer growth, each method including exposing a cell (in vivo, e.g., in a subject, or in vitro) to a compound disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a subject an effective amount of a compound disclosed herein.

In another embodiment, the disclosed compounds are useful for the treatment of a parasitic infection, such as infections caused by protozoan parasites. The proteasome of these parasites is considered to be involved primarily in cell differentiation and replication activities (Paugam et al., Trends Parasitol. 2003, 19 (2): 55-59). Furthermore, *entamoeba* species have been shown to lose encystation capacity when exposed to proteasome inhibitors (Gonzales, et al., Arch. Med. Res. 1997, 28, Spec No: 139-140). In certain such embodiments, the disclosed compounds are useful for the treatment of parasitic infections in humans caused by a protozoan parasite selected from *Plasmodium* sps. (including *P. falciparum, P. vivax, P. malariae,* and *P. ovale,* which cause malaria), *Trypanosoma* sps. (including *T. cruzi,* which causes Chagas' disease, and *T. brucei* which causes African sleeping sickness), *Leishmania* sps. (including *L. amazonensis, L. donovani, L. infantum, L. mexicana,* etc.), *Pneumocystis carinii* (a protozoan known to cause pneumonia in AIDS and other immunosuppressed patients), *Toxoplasma gondii, Entamoeba histolytica, Entamoeba invadens,* and *Giardia lamblia.* In certain embodiments, the disclosed compounds are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona,* and *Neurospora crassa.* Other compounds useful as proteasome inhibitors in the treatment of parasitic diseases are described in WO 98/10779, which is incorporated herein in its entirety.

In certain embodiments, the disclosed compounds inhibit proteasome activity irreversibly in a parasite. Such irreversible inhibition has been shown to induce shutdown in enzyme activity without recovery in red blood cells and white blood cells. In certain such embodiments, the long half-life of blood cells may provide prolonged protection with regard to therapy against recurring exposures to parasites. In certain embodiments, the long half-life of blood cells may provide prolonged protection with regard to chemoprophylaxis against future infection.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., *J. Clin. Invest.* (2003) 111: 1771-1782), therefore suggesting that the ubiquitin-proteasome machinery regulates osteoblast differentiation and bone formation. Therefore, the disclosed compounds may be useful in the treatment and/or prevention of diseases associated with bone loss, such as osteoporosis.

Bone tissue is an excellent source for factors which have the capacity for stimulating bone cells. Thus, extracts of bovine bone tissue contain not only structural proteins which are responsible for maintaining the structural integrity of bone, but also biologically active bone growth factors which can stimulate bone cells to proliferate. Among these latter factors are a recently described family of proteins called bone morphogenetic proteins (BMPs). All of these growth factors have effects on other types of cells, as well as on bone cells, including Hardy, M. H., et al., *Trans Genet* (1992) 8:55-61 describes evidence that bone morphogenetic proteins (BMPs), are differentially expressed in hair follicles during development. Harris, S. E., et al., *J Bone Miner Res* (1994) 9:855-863 describes the effects of TGFβ on expression of BMP-2 and other substances in bone cells. BMP-2 expression in mature follicles also occurs during maturation and after the period of cell proliferation (Hardy, et al. (1992, supra). Thus, compounds of the invention may also be useful for hair follicle growth stimulation.

Finally, the disclosed compounds are also useful as diagnostic agents (e.g., in diagnostic kits or for use in clinical laboratories) for screening for proteins (e.g., enzymes, transcription factors) processed by Ntn hydrolases, including the proteasome. The disclosed compounds are also useful as research reagents for specifically binding the X/MB1 subunit or α-chain and inhibiting the proteolytic activities associated with it. For example, the activity of (and specific inhibitors of) other subunits of the proteasome can be determined Most cellular proteins are subject to proteolytic processing during maturation or activation. Enzyme inhibitors disclosed herein can be used to determine whether a cellular, developmental, or physiological process or output is regulated by the proteolytic activity of a particular Ntn hydrolase. One such method includes obtaining an organism, an intact cell preparation, or a cell extract; exposing the organism, cell preparation, or cell extract to a compound disclosed herein; exposing the compound-exposed organism, cell preparation, or cell extract to a signal, and monitoring the process or output. The high selectivity of the compounds disclosed herein permits rapid and accurate elimination or implication of the Ntn (for example, the 20S proteasome) in a given cellular, developmental, or physiological process.

Administration

Compounds prepared as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can be likewise prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The inhibitor(s) can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more inhibitors(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

These inhibitors(s) may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The concentration of a disclosed compound in a pharmaceutically acceptable mixture will vary depending on several factors, including the dosage of the compound to be administered, the pharmacokinetic characteristics of the compound(s) employed, and the route of administration. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

Another aspect of the invention provides a conjoint therapy wherein one or more other therapeutic agents are administered with the protease inhibitor. Such conjoint treatment may be achieved by way of the simultaneous, sequential, or separate dosing of the individual components of the treatment.

In certain embodiments, a compound of the invention is conjointly administered with a chemotherapeutic. Suitable chemotherapeutics may include, natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates (busulfan), nitrosoureas (carmustine (BCNU) and analogs, streptozocin), trazenes—dacarbazine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors (anastrozole, exemestane, and letrozole); and platinum coordination complexes (cisplatin, carboplatin), procarbazine, hydroxyurea, mitotane, aminoglutethimide; hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a compound of the invention is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In certain embodiments, a compound of the invention is conjointly administered with an immunotherapeutic agent. Suitable immunotherapeutic agents may include, but are not limited to, cyclosporine, thalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

EXEMPLIFICATION

Scheme 1: Synthesis of Example 1

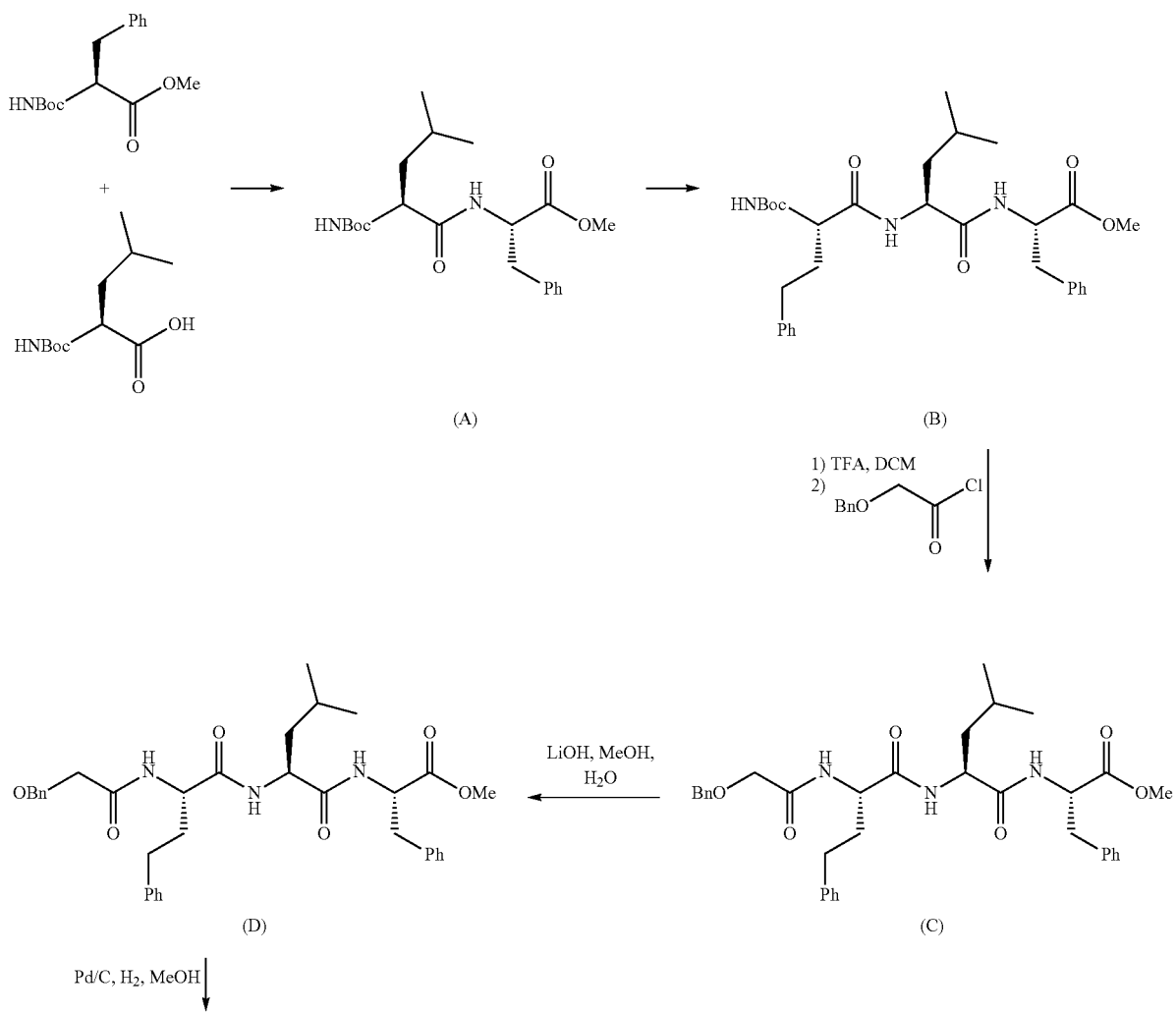

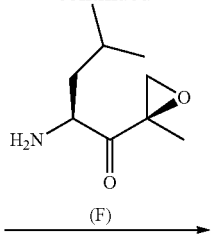
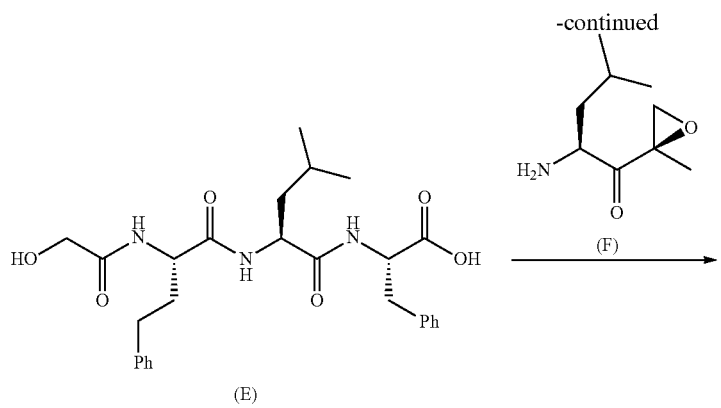

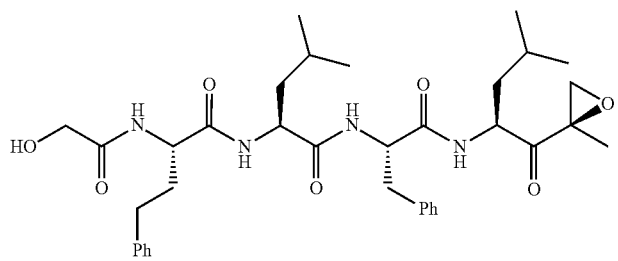

Synthesis of (B)

To a solution of NBoc leucine (50.0 mmol, 11.56 g) and phenylalanine methyl ester (50.0 mmol, 10.78 g) in 500 mL of DMF was added HOBT (10.81 g, 80.0 mmol) and DIEA (200.0 mmol, 25.85 g, 35 mL). The mixture was cooled to 0° C. in an ice-water bath and BOP (80.0 mmol, 35.38 g) was added in several portions over five minutes. The reaction was placed under an atmosphere of argon and stirred overnight. The reaction was diluted with brine (1000 mL) and extracted with EtOAc (5×200 mL). The organic layers were combined and washed with water (10×100 mL) and brine (2×150 mL) and dried over $MgSO_4$. The $MgSO_4$ was removed by filtration and the volatiles removed under reduced pressure to give (A) (18.17 g). To a 50 mL 0° C. cooled solution of 80% TFA/DCM was added BocNHLeuPheOMe (45.86 mmol, 18.0 g). The solution was stirred and allowed to warm to room temperature over 2 hr. The volatiles were removed under reduced pressure to give an oil. To this oil was added BocNHhPhe (45.86 mmol, 12.81 g), DMF (500 mL), HOBT (73.37 mmol, 9.91 g) and DIEA (183.44 mmol, 23.70 g, 32.0 mL). The mixture was cooled to 0° C. in an ice-water bath and BOP (73.37 mmol, 32.45 g) was added in several portions over five minutes. The reaction was placed under argon and allowed to warm to room temperature overnight. The reaction was diluted with $H_2O$ (1500 mL) and extracted with DCM (5×300 mL). The organic layers were combined and washed with $H_2O$ (6×300 mL) and brine (1×300 mL) and dried over $MgSO_4$. The $MgSO_4$ was removed by filtration and the volatiles removed under reduced pressure to give a yellow solid. To the solid was added 200 mL of 95% EtOH and the mixture was heated to 65° C. to dissolve all of the solids. The solution was then added to 1000 mL of chilled $H_2O$ and the resulting precipitate collected to give (B) (21.59 g).

Synthesis of (C)

Compound (B) (1.47 mmol, 0.81 g) was mixed with TFA/DCM (80%) and stirred at room temperature for 1 hr, at which time the mixture was concentrated and placed under high vacuum for 2 hr giving the TFA salt of the tri-peptide amine (Q). To a 0° C. solution of the TFA salt (1.47 mmol) in DMF (10 mL) was added DIEA (4.4 mmol, 0.77 mL) followed by benzyloxyacetyl chloride (2.21 mmol, 0.343 mL). The reaction was allowed to warm to RT while stirring for 2 hr under an atmosphere of nitrogen. The mixture was diluted with brine (15 mL) and extracted with EtOAc (3×15 mL). The organic layers were combined, washed with $H_2O$ (2×15 mL), brine (1×15 mL) and dried over $Na_2SO_4$. The $Na_2SO_4$ was removed by filtration and the volatiles removed under reduced pressure. The crude material was purified by flash chromatography to afford (C) (0.83 g).

Synthesis of (D)

To a slurry of (C) (1.38 mmol, 0.830 g) in 28 mL of 3:1 MeOH/$H_2O$ cooled to 0° C. was added LiOH (13.8 mmol, 0.331 g). After 18 hr at 5° C., the reaction was quenched with 20 mL sat. $NH_4Cl$ and diluted further with 150 mL $H_2O$. The pH of the reaction mixture was adjusted to 2 with 1N HCl and the solids were collected by filtration to give (D) (0.900 g).

Synthesis of (E)

Compound (D) (0.17 mmol, 0.10 g) was dissolved in MeOH (10 mL) and Pd—C (5%, 0.08 g) was added, and the reaction mixture stirred under 1 atmosphere of $H_2$ at room temperature for 2 hr. The mixture was then purged with argon, filtered through Celite, and concentrated to provide (E).

Synthesis of Compound 1

To a stirred solution of (F) [see: Bioorg. Med. Chem. Letter 1999, 9, 2283-88] (0.164 mmol) in DMF (2 mL) was added (E) (0.17 mmol), DIEA (0.652 mmol, 0.114 mL), and HOBT (0.266 mmol, 0.036 g). The mixture was cooled to 0° C. in an ice bath and BOP (0.262 mmol, 0.116 g) was added in several portions. The mixture was stirred at 5° C. under an atmosphere of argon overnight. The reaction was diluted with brine (15 mL) and extracted with EtOAc. The organic layer was washed with water, sat. $NaHCO_3$, and brine and dried over anhydrous $MgSO_4$. The $MgSO_4$ was removed by filtration and the volatiles removed under reduced pressure. The crude material was purified by preparative HPLC to afford compound 1 ($IC_{50}$ 20S CT-L<50 nM, $IC_{50}$ Cell-Based CT-L<100 nM)

Scheme 2: Synthesis of Example 2

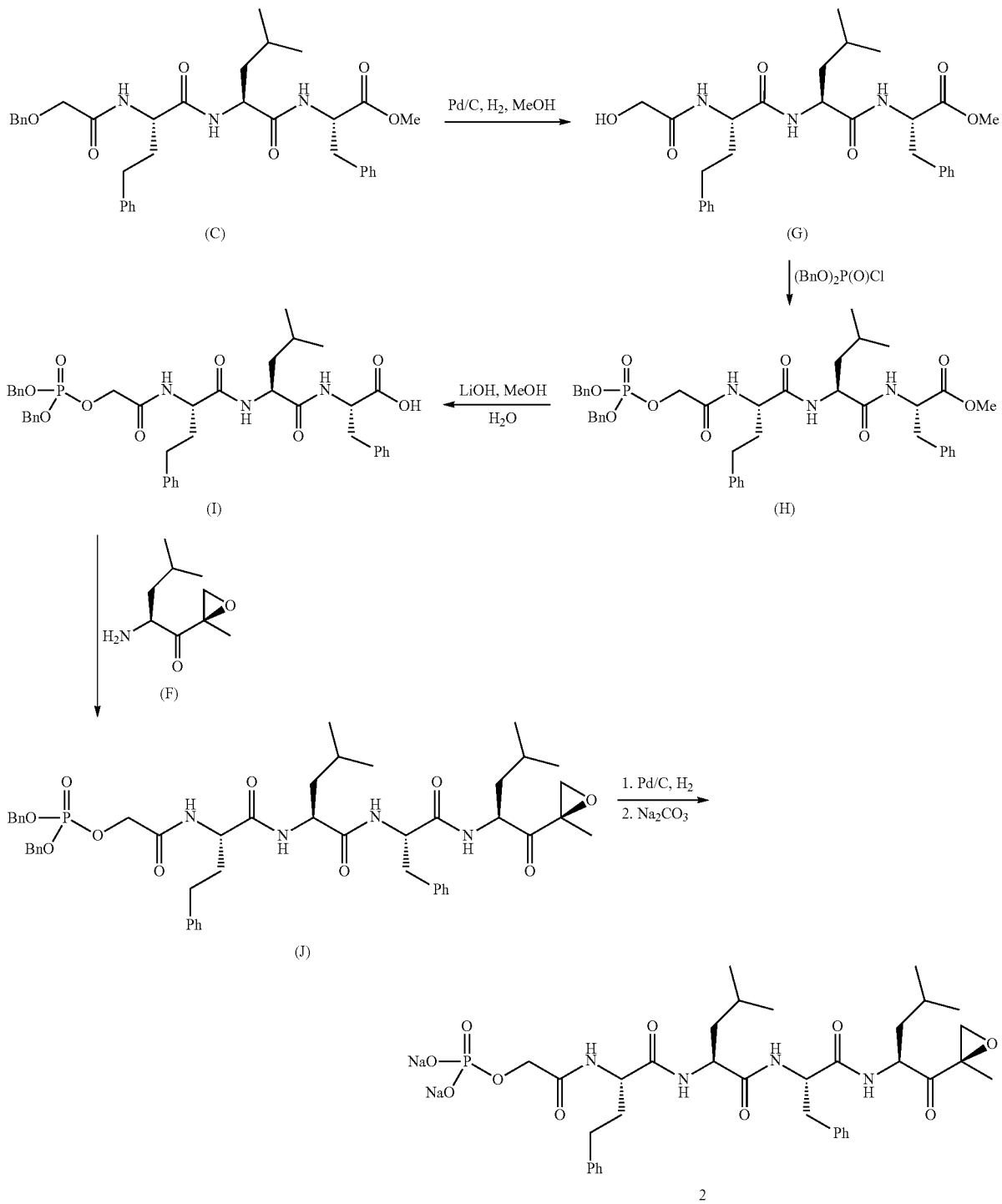

Synthesis of (G)

Compound (C) (1.0 mmol, 0.601 g) was dissolved in MeOH (25 mL), Pd—C (10%, 600 mg) was added and the reaction mixture was stirred under 1 atmosphere of $H_2$ at room temperature for 48 hr. The mixture was then purged with argon, filtered through Celite, and concentrated to provide (G) (600 mg).

Synthesis of (H)

To a 0° C. solution of (G) (1.0 mmol, 0.511 g) in DCM (40 mL) was added DIEA (2.0 mmol, 0.348 mL) and dibenzylphosphoryl chloride (2.0 mmol, 0.593 g) and the mixture was allowed to stir overnight at room temperature under an atmosphere of nitrogen. The reaction was then concentrated under vacuum and the crude material purified by flash chromatography to afford (H) (0.181 g).

Synthesis of (I)

To a slurry of (H) (0.11 mmol, 0.090 g) in 4 mL of 3:1 MeOH/H$_2$O cooled to 0° C. was added LiOH (1.6 mmol, 0.4 mL, 4 M aq.). After 45 minutes at 5° C., the reaction was quenched with 10 mL sat. NH$_4$Cl. The pH of the reaction mixture was adjusted to 2 with 1 N HCl and extracted with EtOAc. The organic layer was washed with water and brine and dried over anhydrous MgSO$_4$. The MgSO$_4$ was removed by filtration and the volatiles removed under reduced pressure to give (I).

Synthesis of (J)

To a stirred solution of (F) [see: Bioorg. Med. Chem. Letter 1999, 9, 2283-88] (0.082 mmol) in DMF (2 mL) was added (I) (0.082 mmol, 0.062 g), DIEA (0.328 mmol, 0.057 mL) and HOBT (0.133 mmol, 0.018 g). The mixture was cooled to 0° C. in an ice bath and BOP (0.131 mmol, 0.058 g) was added in several portions. The mixture was then stirred at 5° C. under an atmosphere of argon overnight. The reaction was diluted with H$_2$O (15 mL) and (J) was collected by filtration (0.081 g).

Synthesis of Compound 2

To a solution of (J) (0.005 mmol, 0.005 g) in THF (1 mL) was added 4 drops of H$_2$O and 10% Pd/C (5 mg). The mixture was stirred under H$_2$ at room temperature for 1 hr, filtered through Celite, and the filtrate was treated with Na$_2$CO$_3$ (0.263 g in 3 mL H$_2$O). The solids were collected by filtration and placed under high vacuum to give compound 2 (0.004 g).

Scheme 3: Synthesis of Example 3

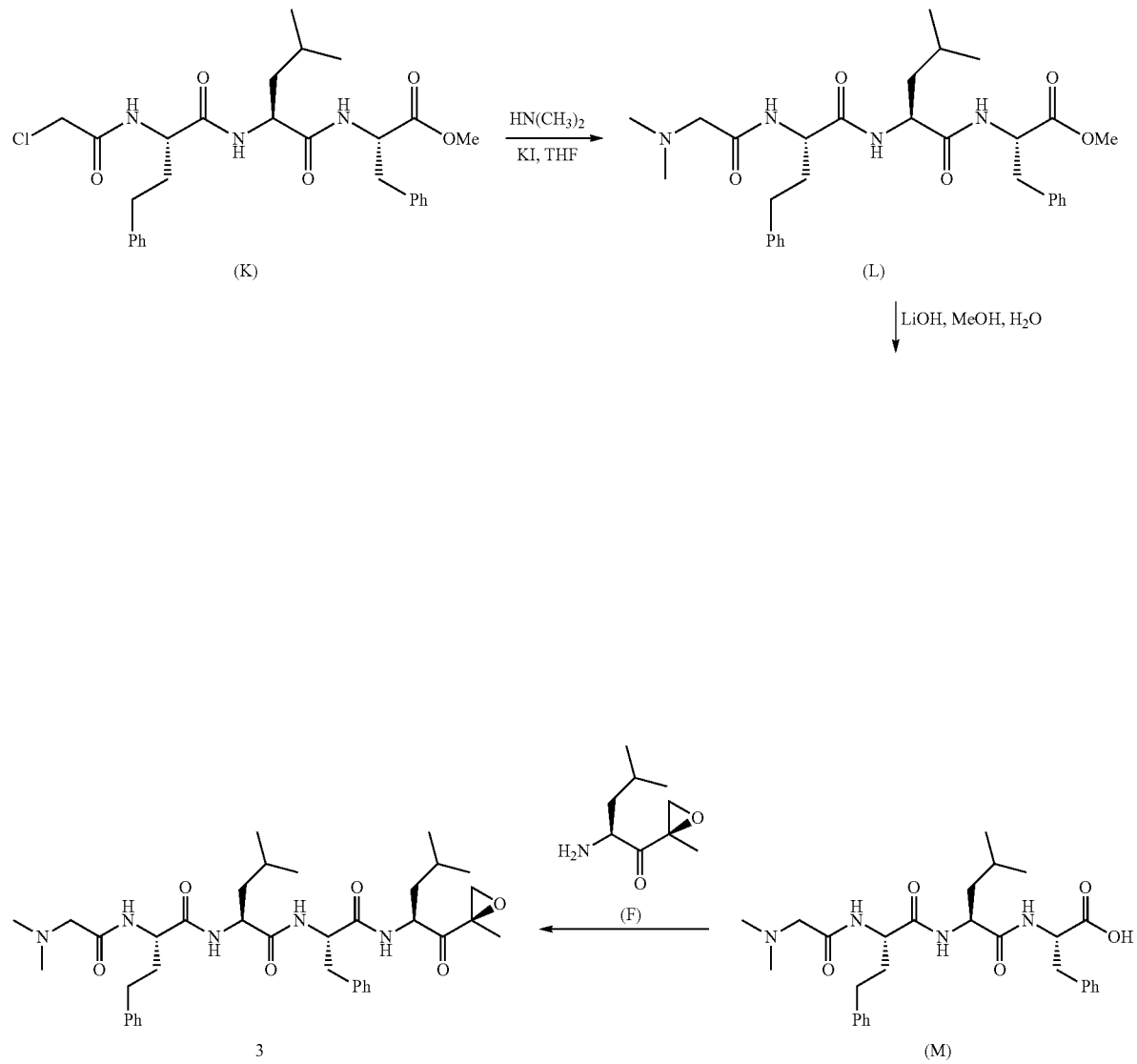

Synthesis of (L)

To a solution of (K) (0.19 mmol, 0.10 g) in THF (20 mL) was added KI (0.038 mmol, 0.0063 g), dimethylamine (0.456 mmol, 0.228 mL, 2M in THF) and the mixture was stirred overnight under an atmosphere of nitrogen. The volatiles were removed under reduced pressure and the crude material was taken up in EtOAc (15 mL), washed with H$_2$O (2×10 mL) and brine (2×10 mL), and dried over MgSO$_4$. The MgSO$_4$ was removed by filtration and the volatiles removed under reduced pressure to give (L) (0.100 g).

Synthesis of (M)

To a slurry of (L) (0.186 mmol, 0.100 g) in 4 mL of 3:1 MeOH/H$_2$O cooled to 0° C. was added LiOH (1.86 mmol, 0.045 g). After 12 hr at 5° C., the reaction was quenched with 20 mL sat. NH$_4$Cl and diluted further with 10 mL H$_2$O. The pH of the reaction mixture was adjusted to 3 with 1 N HCl, extracted with CHCl$_3$ (3×15 mL), and dried over MgSO$_4$. The MgSO$_4$ was removed by filtration and the volatiles were removed under reduced pressure to give (M).

Synthesis of Compound 3

To a stirred solution of (F) [see: Bioorg. Med. Chem. Letter 1999, 9, 2283-88] (0.082 mmol) in DMF (1 mL) was added (M) (0.021 mmol), DIEA (0.28 mmol, 0.05 mL) and HOBT (0.133 mmol, 0.018 g). The mixture was cooled to 0° C. in an ice bath and BOP (0.131 mmol, 0.058 g) was added in several portions. The mixture was stirred at 5° C. under an atmosphere of argon overnight. The reaction was then diluted with brine (15 mL) and extracted with EtOAc. The organic layer was washed with water, sat. NaHCO$_3$, and brine and dried over anhydrous MgSO$_4$. The MgSO$_4$ was removed by filtration and the volatiles removed under reduced pressure to afford compound 3 (IC$_{50}$ 20S CT-L<100 nM; Cell-Based CT-L<100 nM).

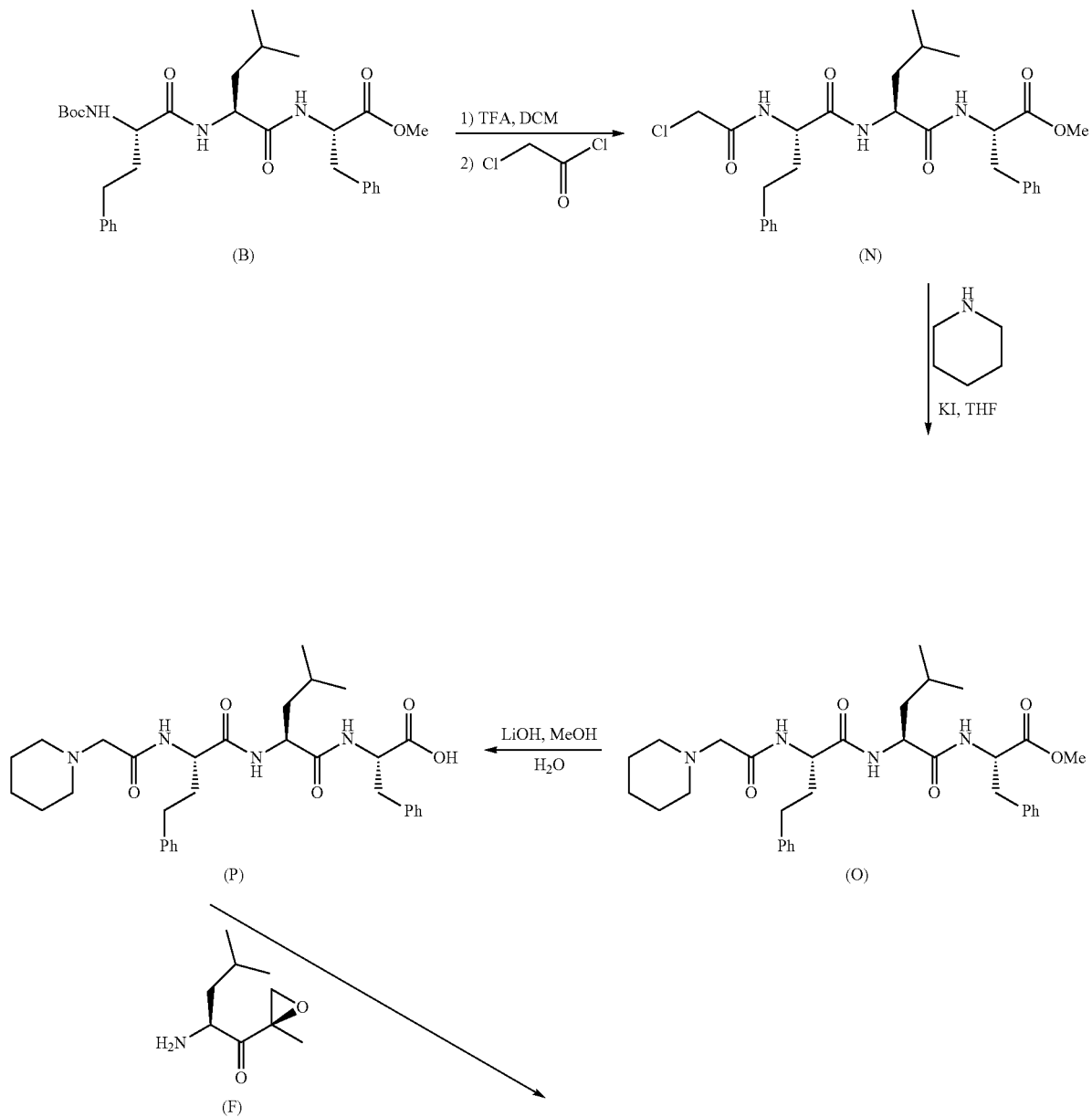

Scheme 4: Synthesis of Example 4

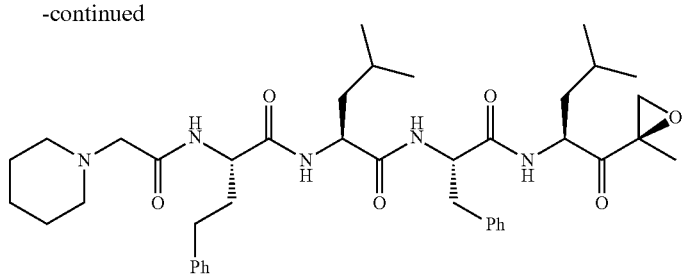

4

Synthesis of (N)

Compound (B) (1.80 mmol, 1.0 g) was mixed with TFA/DCM (80%) and was stirred at room temperature for 1 hr, at which time the mixture was concentrated and placed under high vacuum for 2 hr giving the TFA salt of the tri-peptide amine. To a 0° C. solution of the TFA salt (1.80 mmol) in DMF (10 mL) was added DIEA (3.6 mmol, 0.7 mL) followed by chloroacetyl chloride (2.7 mmol, 0.215 mL). The reaction was allowed to warm to RT while stirring overnight under an atmosphere of nitrogen. The mixture was then diluted with brine (15 mL) and extracted with EtOAc (3×15 mL). The organic layers were combined, washed with $H_2O$ (2×15 mL) and brine (2×15 mL) and dried over $Na_2SO_4$. The $Na_2SO_4$ was removed by filtration and the volatiles removed under reduced pressure. The crude material was suspended in EtOAc and filtered to give (N) (0.640 g)

Synthesis of (O)

To a solution of (N) (0.094 mmol, 0.050 g) in THF (10 mL) was added KI (0.019 mmol, 0.0032 g) and piperidine (0.113 mmol, 0.0096 g) and the mixture stirred overnight under an atmosphere of nitrogen. The volatiles were removed under reduced pressure and the crude material taken up in EtOAc (15 mL), washed with $H_2O$ (2×10 mL) and brine (2×10 mL) and dried over $MgSO_4$. The $MgSO_4$ was removed by filtration and the volatiles removed under reduced pressure to give (O).

Synthesis of (P)

To a slurry of (O) (0.094 mmol) in 4 mL of 3:1 MeOH/$H_2O$ cooled to 0° C. was added LiOH (0.94 mmol, 0.023 g). After 12 hr at 5° C. the reaction was quenched with 20 mL sat. $NH_4Cl$ and diluted further with 10 mL $H_2O$. The pH of the reaction mixture was adjusted to 3 with 1 N HCl, extracted with DCM (3×15 mL), and dried over $MgSO_4$. The $MgSO_4$ was removed by filtration and the volatiles were removed under reduced pressure to give (P).

Synthesis of Compound 4

To a stirred solution of (F) [see: Bioorg. Med. Chem. Letter 1999, 9, 2283-88] (0.082 mmol) in DMF (2 mL) was added (P) (0.082 mmol, 0.046 g), DIEA (0.328 mmol, 0.057 mL) and HOBT (0.133 mmol, 0.018 g). The mixture was cooled to 0° C. in an ice bath and BOP (0.131 mmol, 0.058 g) was added in several portions. The mixture was stirred at 5° C. under an atmosphere of argon overnight. The reaction was then diluted with $H_2O$ (15 mL) and extracted with EtOAc. The organic layer was washed with water, sat. $NaHCO_3$, and brine and dried over anhydrous $MgSO_4$. The $MgSO_4$ was removed by filtration and the volatiles removed under reduced pressure to give compound 4 (0.034 g) ($IC_{50}$ 20S CT-L<100 nM; $IC_{50}$ Cell-Based CT-L<100 nM).

Scheme 5: Synthesis of Example 5

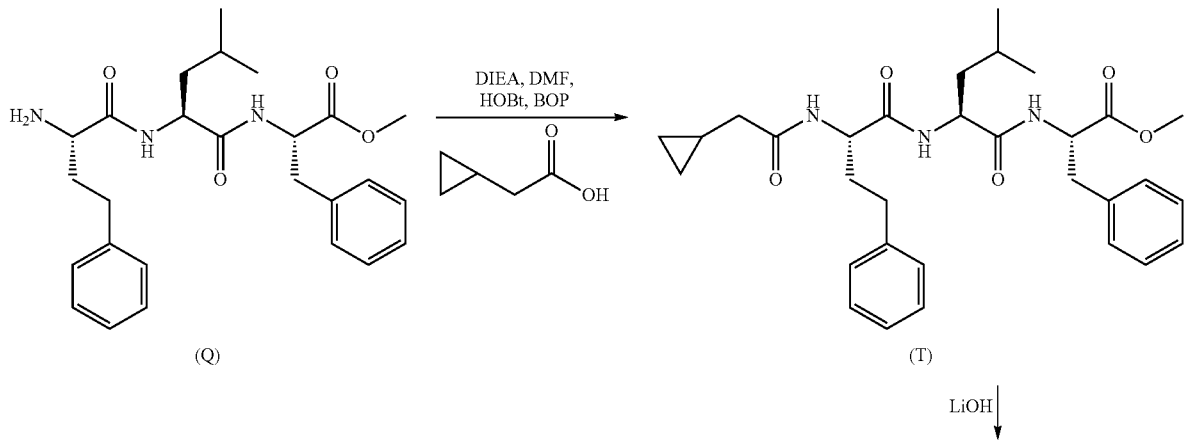

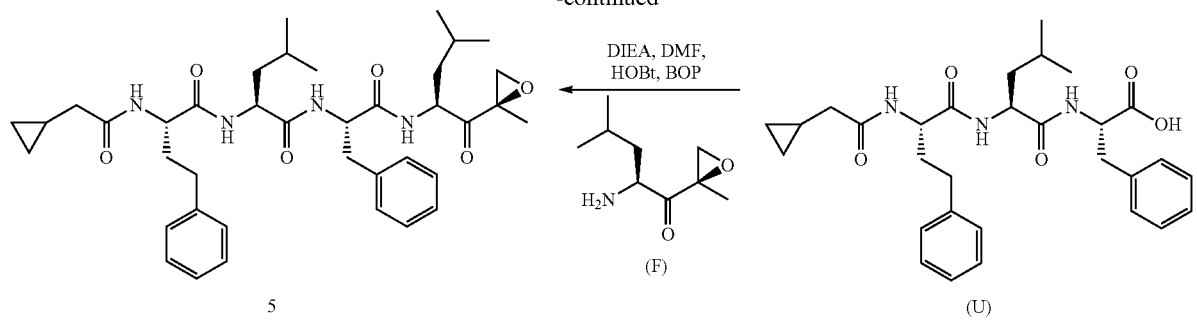

Synthesis of (T)
Compound (T) is obtained by essentially following the procedure for the conversion of (E) to 1 but substituting (O) for (F) and cyclopropylacetic acid for (E).

Synthesis of (U)
Compound (U) is obtained by essentially following the procedure for the conversion of (C) to (D) but substituting (T) for (C).

Synthesis of Compound 5
Compound 5 is obtained by essentially following the procedure for the conversion of (E) to 1 but substituting (U) for (E).

Scheme 6: Synthesis of Example 6

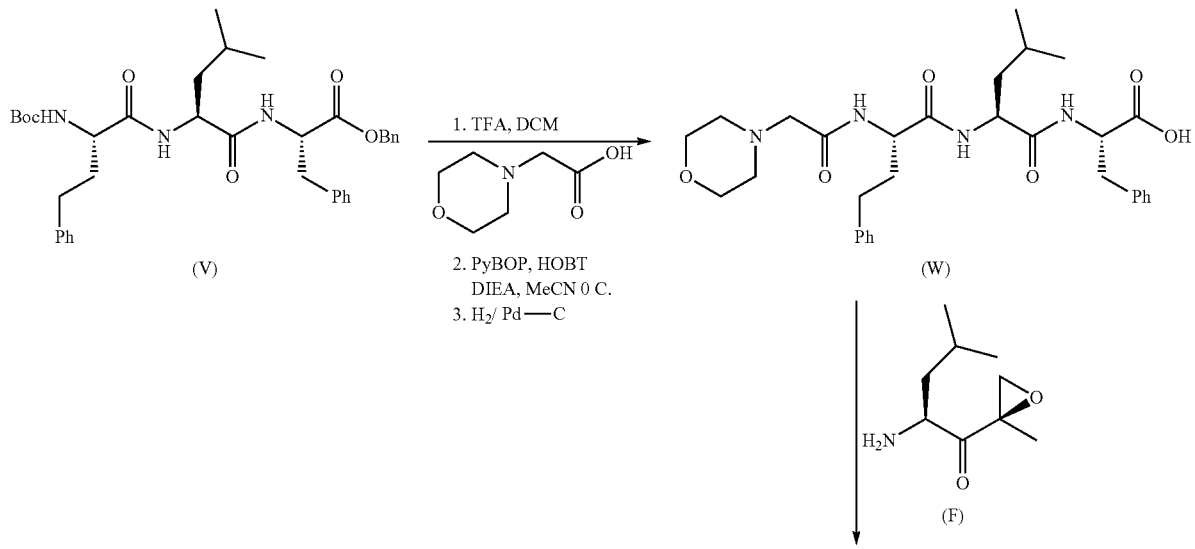

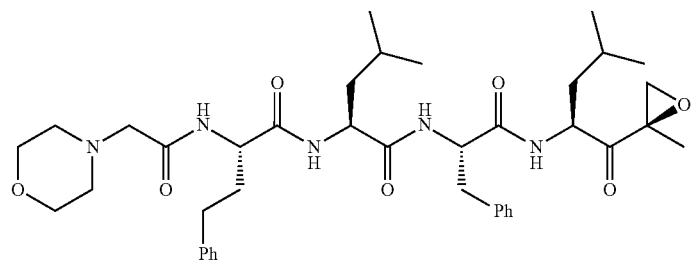

Synthesis of (W)

Compound (V) (0.25 g, 0.39 mmol) was mixed with 12 mL of TFA/DCM (80%) and was stirred at room temperature for 1 hr at which time the mixture was concentrated and placed under high vacuum for 2 hr giving the TFA salt of the tripeptide amine. The crude amine salt was dissolved in 6 mL DMF and 2-morpholino acetic acid (0.074 g, 0.507 mmol) was added followed by DIEA (0.504 g, 0.68 mL, 3.90 mmol). The mixture was cooled to 0° C. in an ice bath and PyBOP (0.32 g, 0.62 mmol) was added and stirred under an atmosphere of argon while warming to room temperature overnight. The mixture was diluted with brine (50 mL) and extracted with EtOAc (5×20 mL). The organic layers were combined, washed with sat. NaHCO$_3$ (5×15 mL) and brine (1×25 mL) and dried over MgSO$_4$. The MgSO$_4$ was removed by filtration and the volatiles removed under reduced pressure to give the intermediate ester (0.195 g). To (0.150 g, 0.23 mmol) of the intermediate ester was added 10% Pd/C (0.05 g) followed by 5 mL of 1:1 mixture of MeOH and EtOAc and the mixture was placed under an atmosphere of hydrogen. After 2 hr, the contents were filtered through a plug of Celite and concentrated under vacuum to give (W) (0.12 g).

Synthesis of Compound 6

To a stirred solution of (F) [see: Bioorg. Med. Chem. Letter 1999, 9, 2283-88] (1.3 eq., 0.27 mmol, 0.083 mg) in MeCN (5 mL) was added (W) (1 eq., 0.17 mmol, 0.10 g), DIEA (10 eq., 1.73 mmol, 0.30 mL) and HOBT (1.6 eq., 0.27 mmol, 0.037 mg). The mixture was cooled to 0° C. in an ice bath and PyBOP (1.6 eq., 0.27 mmol, 0.14 g) was added in several portions. The mixture was stirred at 5° C. under an atmosphere of argon overnight after which, the reaction was diluted with sat. NaCl and extracted with EtOAc. The organic layer was washed with water and brine and dried over anhydrous MgSO$_4$ and concentrated to a paste. The crude material was dissolved in a minimum amount of MeOH and slowly added to rapidly stirred, 0° C. chilled water (100 mL). Compound 6 was then isolated by filtration (0.080 g).

Scheme 7: Synthesis of Example 7

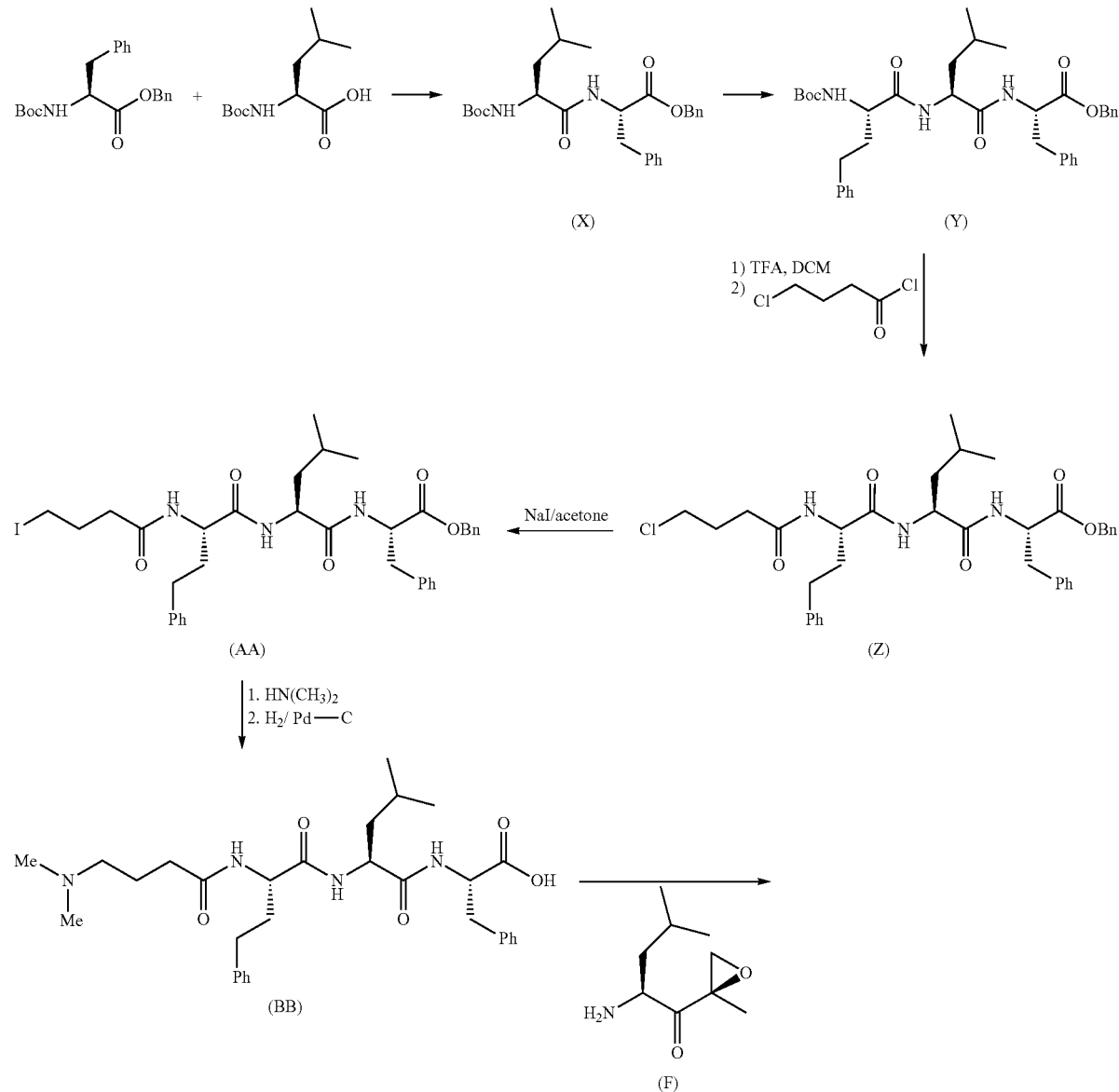

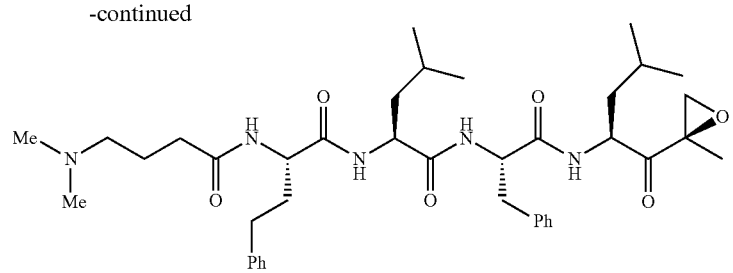

7

Synthesis of (X)

To a solution of NBoc leucine (19.81 g, 85.67 mmol, 1.0 eq) and phenylalanine benzyl ester (25.0 g, 85.67 mmol, 1.0 eq.) in 900 mL of MeCN was added DIEA (44.29 g, 60 mL, 342.68 mmol, 4.0 eq.) and the mixture cooled to 0° C. in an ice bath. To this mixture was added HOBT (18.52 g, 137.08 mmol, 1.6 eq) followed by PyBOP (71.33 g, 137.08 mmol, 1.6 eq) which was added in several portions over five minutes. The reaction was placed under an atmosphere of argon and stirred overnight. The volatiles were removed under reduced pressure and the remaining material was taken up in 500 mL of EtOAc and washed with sat. $NaHCO_3$, $H_2O$, and brine and dried over $MgSO_4$. The $MgSO_4$ was removed by filtration and the volatiles removed under reduced pressure to give (X).

Synthesis of (Y)

To a 0° C. cooled solution of 70% TFA/DCM (150 mL) was added (X) (25.0 g, 53.35 mmol, 1.0 eq.). The solution was stirred and allowed to warm to room temperature over 2 hr at which time the mixture was concentrated and placed under high vacuum for 2 hr giving the TFA salt of the di-peptide amine. To the resulting oil was added BocNHhPhe (14.68 g, 53.35 mmol, 1.0 eq.), 550 mL of MeCN, and DIEA (27.58 g, 37.2 mL, 213.4 mmol, 4.0 eq.) and the mixture was cooled to 0° C. in an ice bath. To the cooled mixture was added HOBT (11.53 g, 85.36 mmol, 1.6 eq.) followed by PyBOP (44.42 g, 85.36 mmol, 1.6 eq.) which was added in several portions over five minutes. The reaction was placed under argon and allowed to warm to room temperature overnight at which time a white precipitate had formed. The reaction mixture was cooled and the solids were collected by filtration and then washed with cold MeCN to give (Y) (24.86 g).

Synthesis of (Z)

Compound (Y) (0.023 mol, 14.5 g) was mixed with TFA/DCM (80%) and stirred at room temperature for 1 hr at which time the mixture was concentrated and placed under high vacuum for 2 hr giving the TFA salt of the tri-peptide amine. To a solution of the TFA salt (0.023 mol, 1 eq.) in MeCN (120 mL) was added 4-chlorobutyryl chloride (1.2 eq., 0.028 mol, 0.32 mL) and DIEA (4 eq., 0.092 mol, 16 mL). The mixture was stirred at room temperature for 2 hr and then concentrated and purified by flash chromatography to afford (Z) (8 g).

Synthesis of (AA)

To a solution of (Z) (1 eq., 0.095 mmol, 60 mg) in dry acetone (8 mL) was added NaI (5 eq., 0.47 mmol, 70.5 mg). The mixture was stirred at reflux under an atmosphere of nitrogen overnight. The reaction mixture was then concentrated to dryness and the residue taken up in DCM. The organic layer was washed with water and brine, dried over anhydrous $MgSO_4$, and concentrated to give (AA) as a yellow solid (50 mg).

Synthesis of (BB)

To a solution of (AA) (30 mg, 0.041 mmol) in THF (2 mL) was added dimethylamine (1.2 eq., 0.05 mmol, 2M in THF, 25 μL) and DIEA (1 eq., 0.041 mmol, 7.2 μL). The mixture was stirred at room temperature overnight and concentrated to dryness. The residue was taken up in ethyl acetate and washed with water and brine, dried over anhydrous $MgSO_4$, and concentrated to give an oil product. The crude ester was dissolved in MeOH/EtOAc (1:1, 10 mL) and Pd—C (5%, 20 mg) was added and the reaction mixture stirred under 1 atmosphere of $H_2$ at room temperature for 2 hr. The mixture was then purged with argon, filtered through Celite, and concentrated to provide (BB) (21 mg).

Synthesis of Compound 7

To a stirred solution of (F) [see: Bioorg. Med. Chem. Letter 1999, 9, 2283-88] (1.2 eq., 0.054 mmol) in DMF (3 mL) was added (BB) (1 eq., 0.045 mmol, 21 mg), DIEA (4 eq., 0.18 mmol, 31 μL), and HOBT (1.6 eq., 0.072 mmol, 10 mg). The mixture was cooled to 0° C. in an ice bath and PyBOP (1.6 eq., 0.072 mmol, 37 mg) was added in several portions. The mixture was then stirred at 5° C. under an atmosphere of nitrogen overnight. The reaction was then diluted with sat. NaCl and extracted with EtOAc. The organic layer was washed with water and brine and dried over anhydrous $MgSO_4$ and concentrated to an oil that was purified by flash chromatography to afford compound 7 (16.7 mg) ($IC_{50}$ 20S CT-L<50 nM, Cell-Based CT-L<150 nM).

Scheme 8: Synthesis of Example 8

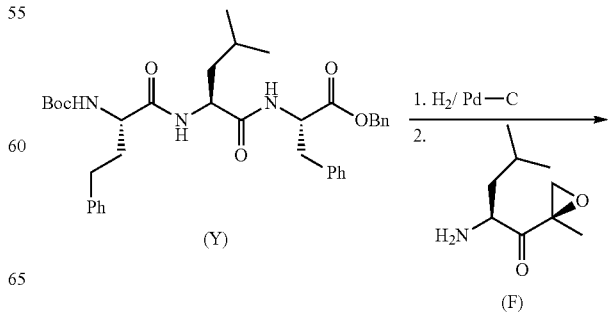

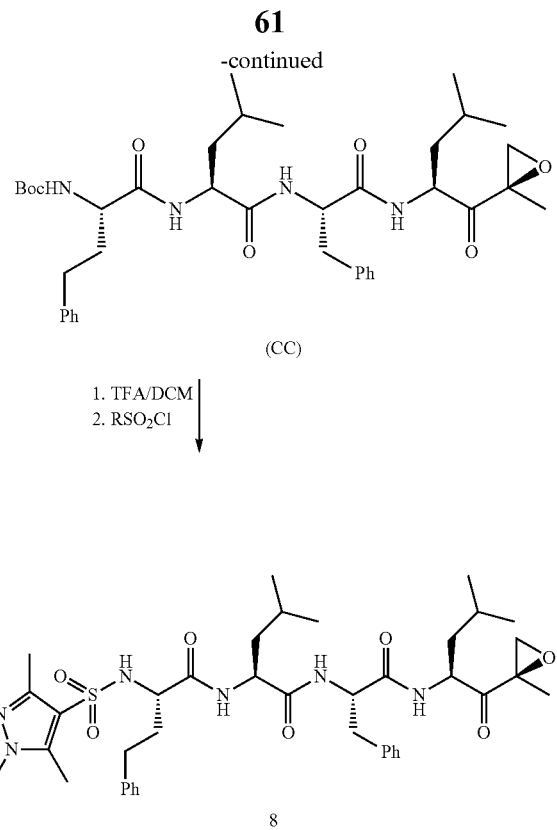

(CC)

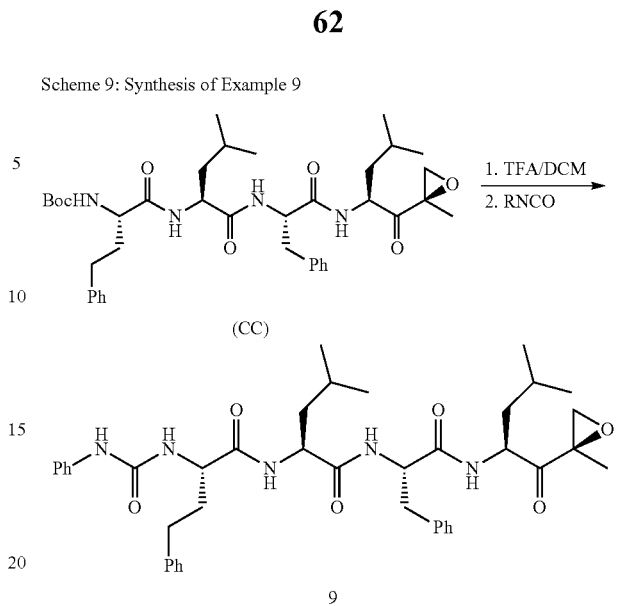

Scheme 9: Synthesis of Example 9

(CC)

9

Synthesis of Compound 9

Compound (CC) (63.7 mg, 0.092 mmol) was mixed with TFA/DCM (80%) and was stirred at room temperature for 1 hr at which time the mixture was concentrated and placed under high vacuum for 2 hr giving the TFA salt of the tetrapeptide amine. To a DCM solution of the TFA salt was added phenyl isocyanate (1.5 eq., 0.14 mmol, 15 µL) and DIEA (3 eq., 0.276 mmol, 50 µL) and the mixture was stirred at room temperature overnight. The crude mixture was concentrated to dryness and the residue was taken up in EtOAc. The organic layer was washed with water and brine, dried over anhydrous MgSO$_4$, and concentrated to an oil that was purified by flash chromatography to afford compound 9 (2.8 mg).

8

Synthesis of (CC)

Compound (Y) (1.55 g, 0.0023 mol) was dissolved in MeOH/EtOAc (1:1, 40 mL) and Pd—C (5%, 500 mg) was added. The mixture was stirred at room temperature under hydrogen for 2 hr, and then filtered through Celite and concentrated to get the carboxylic acid intermediate. To a stirred solution of (F) [see: Bioorg. Med. Chem. Letter 1999, 9, 2283-88] (1.2 eq., 2.55 mmol, 436 mg) in DMF (50 mL) was added the carboxylic acid intermediate (1 eq., 2.12 mmol, 1.24 g), DIEA (4 eq., 8.48 mmol, 1.5 mL) and HOBT (1.6 eq., 3.39 mmol, 458 mg). The mixture was cooled to 0° C. in an ice bath and PyBOP (1.6 eq., 3.39 mmol, 1.76 g) was added in several portions. The mixture was stirred at 5° C. under an atmosphere of nitrogen overnight. The reaction was diluted with sat. NaCl and extracted with EtOAc. The organic layer was washed with water and brine and dried over anhydrous MgSO$_4$ and concentrated to an oil that was purified by flash chromatography to afford (CC) (356 mg).

Synthesis of Compound 8

Compound (CC) (23.6 mg, 0.034 mmol) was mixed with TFA/DCM (80%) and was stirred at room temperature for 1 hr at which time the mixture was concentrated and placed under high vacuum for 2 hr giving the TFA salt of the tetrapeptide amine. To a DCM solution of the TFA salt was added 1,3,5-trimethyl-1-H-pyrazole-4-sulfonyl chloride (1.2 eq., 0.041 mmol, 8.5 mg) and TEA (4 eq., 0.136 mmol, 26 µL) and the mixture was stirred at room temperature overnight. The crude mixture was concentrated to dryness and the residue was taken up in EtOAc. The organic layer was washed with water and brine, dried over anhydrous MgSO$_4$, and concentrated to an oil that was purified by flash chromatography to afford compound 8 (2 mg) (IC$_{50}$ 20S CT-L<100 nM, Cell-Based CT-L<100 nM)

Scheme 10: Synthesis of Example 10

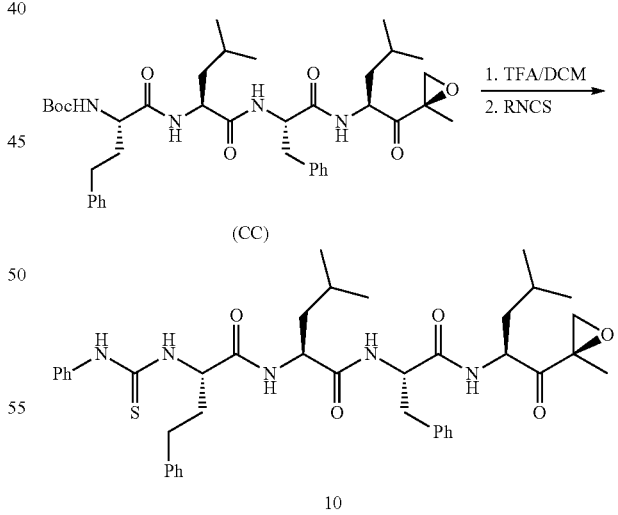

(CC)

10

Synthesis of Compound 10

Compound (CC) (48.5 mg, 0.07 mmol) was mixed with TFA/DCM (80%) and was stirred at room temperature for 1 hr at which time the mixture was concentrated and placed under high vacuum for 2 hr giving the TFA salt of the tetrapeptide amine. To a DCM solution of the TFA salt was added phenyl isothiocyanate (1.5 eq., 0.105 mmol, 20 µL) and DIEA (3 eq., 0.21 mmol, 40 µL) and the mixture was stirred at room temperature overnight. The crude mixture was concentrated to dryness and the residue was taken up in EtOAc. The organic layer was washed with water and brine, dried over anhydrous MgSO$_4$ and concentrated to an oil that was purified by flash chromatography to afford compound 10 (1 mg).

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

All of the above-cited references and publications are hereby incorporated by reference.

We claim:

1. A method for preparing a compound having formula (II), or a pharmaceutically acceptable salt thereof:

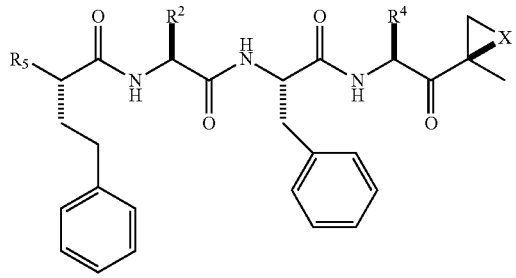
(II)

wherein
X is O;
R² and R⁴ are each isobutyl;
R⁵ is selected from the group consisting of:
(i) —NHC(=O)CH₂OH;
(ii) —NHC(=O)CH₂OP(O)(O⁻Na⁺)₂;
(iii) —NHC(=O)CH₂N(CH₃)₂;
(iv) —NHC(=O)CH₂-(1-piperidyl);
(v) —NHC(=O)CH₂-(cyclopropyl); and
(vi) —NHC(=O)CH₂CH₂CH₂N(CH₃)₂;

the method comprising reacting a first compound, or a salt thereof, having a first formula, which is selected from the group consisting of:

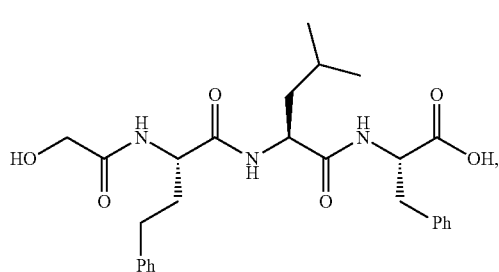

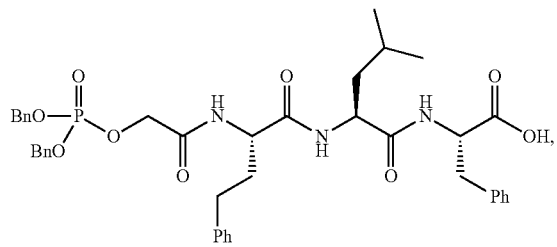

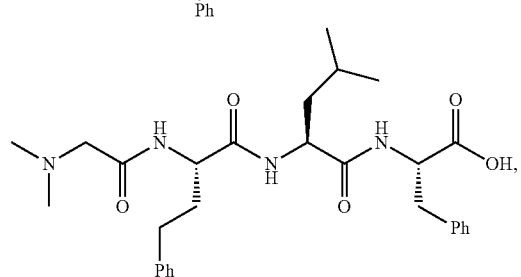

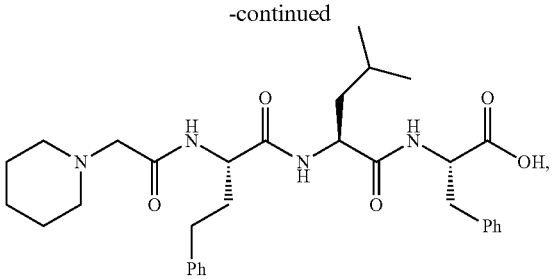

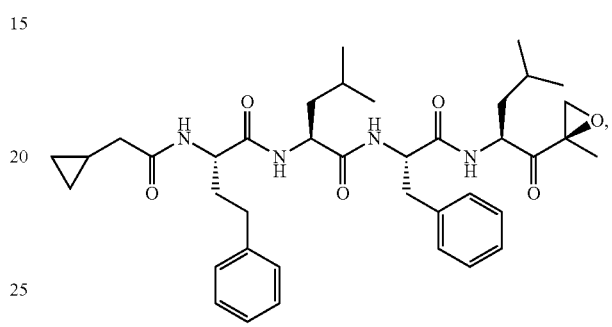

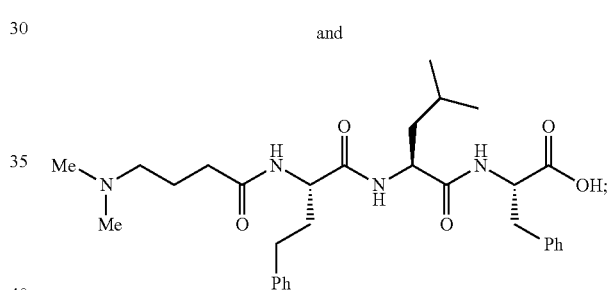

and with a second compound, or a salt thereof, having a second formula:

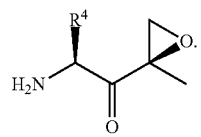

2. The method of claim 1, wherein the first compound has the formula:

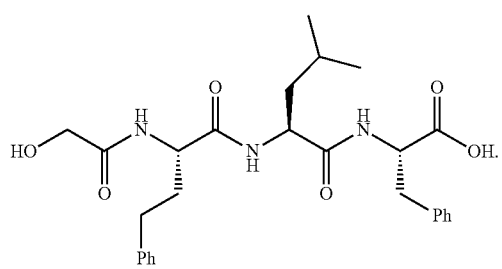

3. The method of claim 1, wherein the first compound has the formula:

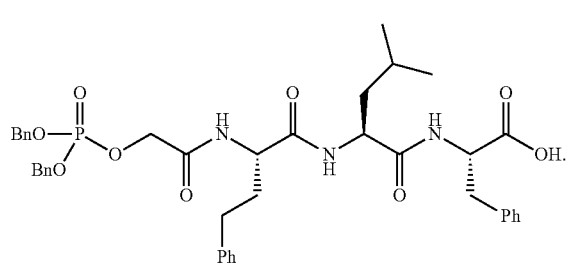

4. The method of claim 1, wherein the first compound has the formula:

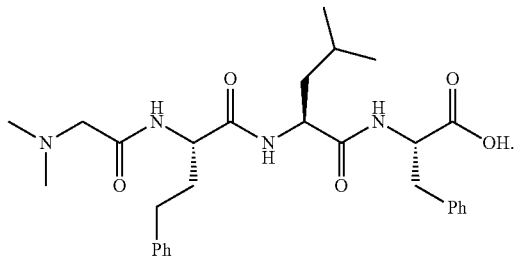

5. The method of claim 1, wherein the first compound has the formula:

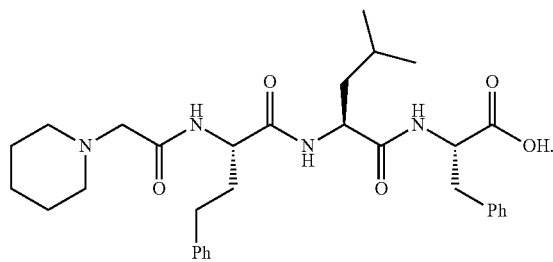

6. The method of claim 1, wherein the first compound has the formula:

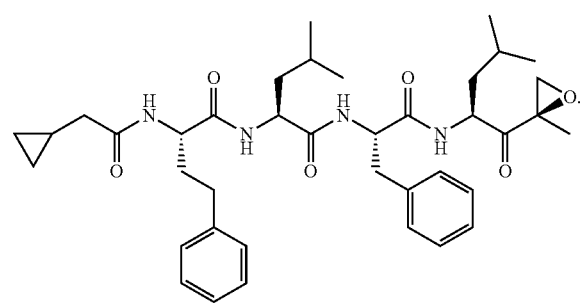

7. The method of claim 1, wherein the first compound has the formula:

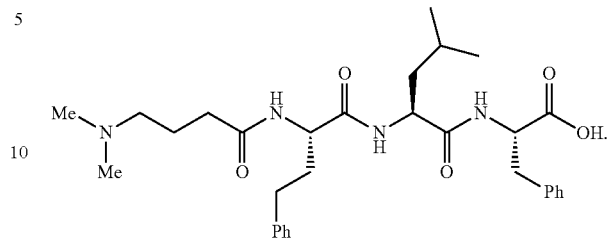

8. The method of claim 1, wherein reacting the first compound with the second compound is carried out in the presence of BOP or PyBOP and HOBt.

9. The method of claim 8, wherein reacting the first compound with the second compound is carried out in the presence of DIEA.

10. The method of claim 1, wherein the method further comprises mixing the compound having formula (I), or a pharmaceutically acceptable salt thereof, with one or more pharmaceutically acceptable carriers to form a composition.

11. The method of claim 10, wherein at least one of the one or more pharmaceutically acceptable carriers is a cyclodextrin.

12. The method of claim 10, wherein at least one of the one or more pharmaceutically acceptable carriers is a substituted or unsubstituted β-cyclodextrin.

13. The method of claim 10, wherein the method further comprises adding an anti-oxidant.

14. The method of claim 13, wherein the anti-oxidant is citric acid.

15. A compound having formula (II), or a pharmaceutically acceptable salt thereof:

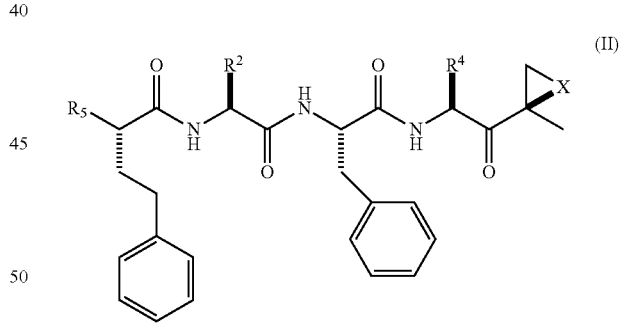

(II)

wherein
X is O;
$R^2$ and $R^4$ are each isobutyl;
$R^5$ is selected from the group consisting of:
(i) —NHC(=O)CH$_2$OH;
(ii) —NHC(=O)CH$_2$OP(O)(O$^-$Na$^+$)$_2$);
(iii) —NHC(=O)CH$_2$N(CH$_3$)$_2$;
(iv) —NHC(=O)CH$_2$-(1-piperidyl);
(v) —NHC(=O)CH$_2$-(cyclopropyl); and
(vi) —NHC(=O)CH$_2$CH$_2$CH$_2$N(CH$_3$)$_2$;

prepared by a process as claimed in claim 1.

16. A composition prepared by a process as claimed in claim 10.

17. A method for preparing a compound having formula (II), or a pharmaceutically acceptable salt thereof:

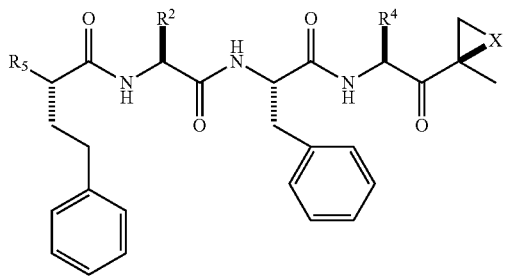

X is O;
R$^2$- and R$^4$ are each isobutyl;
R$^5$ is selected from the group consisting of:
(i)

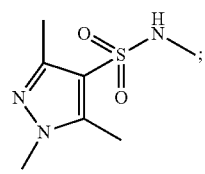

(ii) —NHC(=O)NHPh; and
(iii) —NHC(=S)NHPh; and
the method comprising:
(a) reacting a first compound, or a salt thereof, having a first formula:

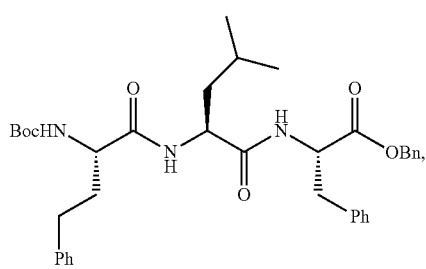

with a second compound, or a salt thereof, having a second formula:

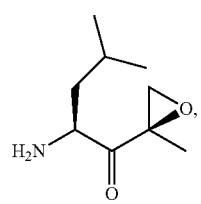

in the presence of H$_2$/Pd/C, to form a third compound, or a salt thereof, having a third formula:

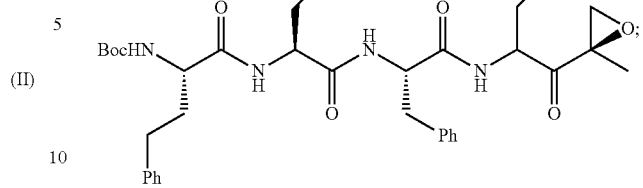

and
(b) reacting the third compound, or a salt thereof, with a fourth compound in the presence of trifluoroacetic acid, wherein the fourth compound is selected from the group consisting of:
(i) 1,3,5-trimethyl-1-H-pyrazole-4-sulfonyl chloride;
(ii) phenyl isocyanate; and
(iii) phenyl isothiocyanate.

18. The method of claim 17, wherein the fourth compound is 1,3,5-trimethyl-1-H-pyrazole-4-sulfonyl chloride.

19. The method of claim 17, wherein the fourth compound is phenyl isocyanate.

20. The method of claim 17, wherein the fourth compound is phenyl isothiocyanate.

21. A compound having formula (II), or a pharmaceutically acceptable salt thereof:

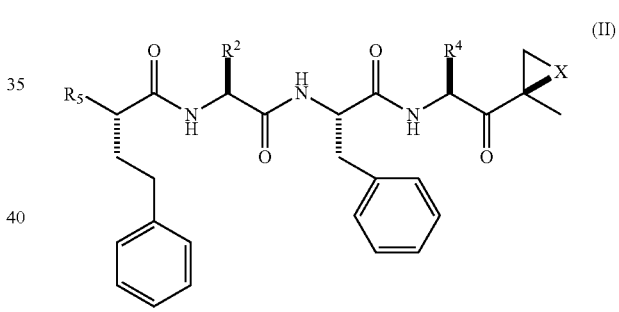

X is O;
R$^2$- and R$^4$ are each isobutyl;
R$^5$ is selected from the group consisting of:
(i)

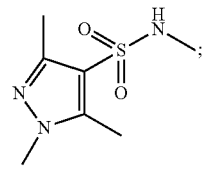

(ii) —NHC(=O)NHPh; and
(iii) —NHC(=S)NHPh;
prepared by a process as claimed in claim 17.

22. The method of claim 17, wherein the method further comprises mixing the compound having formula (I), or a pharmaceutically acceptable salt thereof, with one or more pharmaceutically acceptable carriers to form a composition.

23. The method of claim 22, wherein at least one of the one or more pharmaceutically acceptable carriers is a cyclodextrin.

24. The method of claim 22, wherein at least one of the one or more pharmaceutically acceptable carriers is a substituted or unsubstituted β-cyclodextrin.

25. The method of claim 22, wherein the method further comprises adding an anti-oxidant.

26. The method of claim 25, wherein the anti-oxidant is citric acid.

27. A composition prepared by a process as claimed in claim 22.

* * * * *

UNITED STATES PATENT AND TRADEMARK OFFICE
CERTIFICATE OF CORRECTION

PATENT NO. : 8,324,174 B2
APPLICATION NO. : 13/334372
DATED : December 4, 2012
INVENTOR(S) : Mark S. Smyth et al.

It is certified that error appears in the above-identified patent and that said Letters Patent is hereby corrected as shown below:

Col. 66, lines 46-52 (approximately), that part of the formula reading "  "

should read -- 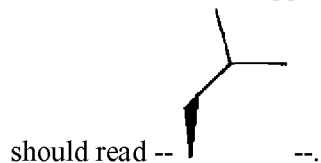 --.

Col. 68, line 61 (approximately), "($O^-Na^+$)$_2$);" should read -- ($O^-Na^+$)$_2$; --.

Col. 69, line 22 (approximately), "$R^2$-" should read -- $R^2$ --.

Col. 70, line 47 (approximately), "$R^2$-" should read -- $R^2$ --.

Signed and Sealed this
Second Day of April, 2013

Teresa Stanek Rea
*Acting Director of the United States Patent and Trademark Office*